United States Patent
Tanishima et al.

(10) Patent No.: US 10,311,239 B2
(45) Date of Patent: Jun. 4, 2019

(54) GENETIC INFORMATION STORAGE APPARATUS, GENETIC INFORMATION SEARCH APPARATUS, GENETIC INFORMATION STORAGE PROGRAM, GENETIC INFORMATION SEARCH PROGRAM, GENETIC INFORMATION STORAGE METHOD, GENETIC INFORMATION SEARCH METHOD, AND GENETIC INFORMATION SEARCH SYSTEM

(71) Applicant: MITSUBISHI SPACE SOFTWARE CO., LTD., Tokyo (JP)

(72) Inventors: Shigeki Tanishima, Tokyo (JP); Nori Matsuda, Tokyo (JP)

(73) Assignee: Mitsubishi Space Software Co., Ltd., Tokyo (JP)

( * ) Notice: Subject to any disclaimer, the term of this patent is extended or adjusted under 35 U.S.C. 154(b) by 648 days.

(21) Appl. No.: 14/779,527

(22) PCT Filed: Feb. 21, 2014

(86) PCT No.: PCT/JP2014/054145
§ 371 (c)(1),
(2) Date: Sep. 23, 2015

(87) PCT Pub. No.: WO2014/156400
PCT Pub. Date: Oct. 2, 2014

(65) Prior Publication Data
US 2016/0048690 A1     Feb. 18, 2016

(30) Foreign Application Priority Data

Mar. 28, 2013  (JP) ................................ 2013-067770

(51) Int. Cl.
*G06F 21/60*   (2013.01)
*G06F 19/22*   (2011.01)
(Continued)

(52) U.S. Cl.
CPC ............ *G06F 21/602* (2013.01); *G06F 19/22* (2013.01); *G06F 19/28* (2013.01); *H04L 9/00* (2013.01);
(Continued)

(58) Field of Classification Search
None
See application file for complete search history.

(56) References Cited

U.S. PATENT DOCUMENTS

| 7,519,031 B2 | 4/2009 | Kayahara |
| 2003/0108021 A1 | 6/2003 | Kayahara |

(Continued)

FOREIGN PATENT DOCUMENTS

| JP | 2003-177992 A | 6/2003 |
| JP | 2008-276550 A | 11/2008 |

(Continued)

OTHER PUBLICATIONS

Boneh et al., "Public Key Encryption with keyword Search", pp. 1-15.

(Continued)

*Primary Examiner* — Henry Tsang
(74) *Attorney, Agent, or Firm* — Birch, Stewart, Kolasch & Birch, LLP

(57) ABSTRACT

An object is to enable to search genetic information in an encrypted state. An encryption apparatus (200) encrypts a target gene which is genetic information to be stored in a storage apparatus and generates an encrypted gene, as well compares a reference gene which is predefined genetic information with the target gene to generate differential information, and generates an encrypted tag which is encrypted by embedding the generated differential information. A data center (400) stores the encrypted gene with related to the encrypted tag in the storage apparatus. A search apparatus (300) generates a search query which is encrypted by embedding the differential information as a search keyword, and sends the generated search query to a data center (400). The data center (400) specifies the encrypted tag including the differential information speci- (Continued)

fied in the search query, extracts the related encrypted gene, and sends the encrypted gene to the search apparatus (300).

22 Claims, 22 Drawing Sheets

(51) Int. Cl.
    *G06F 19/28*     (2011.01)
    *H04L 9/00*     (2006.01)
    *H04L 9/08*     (2006.01)
    *G09C 1/00*     (2006.01)

(52) U.S. Cl.
    CPC .............. *H04L 9/0816* (2013.01); *G09C 1/00* (2013.01); *H04L 2209/24* (2013.01)

(56) References Cited

U.S. PATENT DOCUMENTS

2004/0153255 A1* 8/2004 Ahn ..................... G06F 19/22
    702/20
2008/0270386 A1 10/2008 Ohi et al.
2013/0287210 A1* 10/2013 Matsuda ............... H04L 9/0894
    380/44

FOREIGN PATENT DOCUMENTS

| JP | 2012-73693 A | | 4/2012 | |
|---|---|---|---|---|
| JP | 2012073693 A | * | 4/2012 | |
| JP | WO 2012095973 A1 | * | 7/2012 | ........... H04L 9/0894 |
| WO | WO 2012/095973 A1 | | 7/2012 | |

OTHER PUBLICATIONS

Lewko et al., "Fully Secure Functional Encryption: Attribute-Based Encryption and (Hierarchical) Inner Product Encryption", pp. 1-56.
Minegishi et al., "Implementation of a Privacy-Preserving SNP Search System in Data Outsourcing", DEIM Forum 2013 p. 2-5.
Shimizu et al., A Proposal of a Secure Search Method for Similar Strings in a DAS Model, Journal of the DBSJ, vol. 7, No. 1, Jun. 2008, pp. 13-18.

\* cited by examiner

Fig. 17

USER ID INFORMATION DATABASE

| GROUP NAME | USER NAME | AFFILIATION INFORMATION | VALID TERM |
|---|---|---|---|
| PHARMACEUTICAL COMPANY A | TARO TANAKA | COLD MEDICINE DEPARTMENT/ LABORATORY | 2005/4~ |
| ............ | ............ | ............ | ............ |

Fig. 21

GROUP NAME: PHARMACEUTICAL COMPANY A
USER NAME: *

| MANAGEMENT NO. | PATIENT ID | ENCRYPTED DATA |
|---|---|---|
| 000001 | 12345678 | po8q234ndf09234n |
| 000002 | 98765432 | 84gh4¥sfd78341n# |
| ........ | ........ | ........ |

GROUP NAME: HOSPITAL B
USER NAME: *

| MANAGEMENT NO. | PATIENT ID | ENCRYPTED DATA |
|---|---|---|
| 100001 | 12345678 | 82jd723j9k#s%df4 |
| 100002 | 98765432 | SAME AS 000001 |
| ........ | ........ | ........ |

Fig. 24

ACCESS AUTHORITY MANAGEMENT TABLE

| ACCESSOR INFORMATION | PATIENT ID | TYPE OF DATA | AUTHORIZED OPERATION |
|---|---|---|---|
| TANAKA/PHARMACEUTICAL COMPANY A | 12345678 | ALL | SEARCH/BROWSE |
| TAKAHASHI/HOSPITAL B | 98765432 | ELECTRONIC HEALTH RECORD | BROWSE |
| ............ | ............ | ............ | ............ |

GENETIC INFORMATION STORAGE APPARATUS, GENETIC INFORMATION SEARCH APPARATUS, GENETIC INFORMATION STORAGE PROGRAM, GENETIC INFORMATION SEARCH PROGRAM, GENETIC INFORMATION STORAGE METHOD, GENETIC INFORMATION SEARCH METHOD, AND GENETIC INFORMATION SEARCH SYSTEM

TECHNICAL FIELD

The present invention relates to storage technique to encrypt genetic information which is analyzed information of a genome or a gene that is obtained as a result of analyzing a DNA sequence and to store in a storage apparatus. Further, the present invention relates to a technique to search the genetic information stored using the above storage technique in an encrypted status.

BACKGROUND ART

Recent years, the biotechnology has been extremely developed, and reading ability of a genome sequence has also been developed. Therefore, a cost required for decoding all the genome sequences of one human body is decreased, and the genome sequences of many people are now decoded.

Genetic information including a personal genome sequence and its related information such as manifestation information is said to be ultimate personal information, and disclosure of the information to people other than the owner must be safely carried out. The genetic information which is output from a reading apparatus of a genome DNA and a RNA sequence and analyzed to become meaningful information must be promptly encrypted, so that no one can decipher such information without acceptance of the owner.

There is a searchable encryption scheme according to which while the data stored in the database and the search keyword are in an encrypted status, the data including the search keyword is searchable from the data stored in the database (refer to Non-Patent Literature 1).

In the searchable encryption scheme, upon accumulating data in the database, a search keyword that is assumed to be used for searching the data is extracted as a tag. Then, the data and the tag are respectively encrypted, the encrypted tag is attached to the encrypted data, and the encrypted data with the encrypted tag is stored in the database.

In a case where the data including the search keyword is searched from the data stored in the database, the encrypted search keyword is entered. Then, the encrypted tag corresponding to the encrypted search keyword is searched. If a tag corresponding to the search keyword is found, the data to which the tag is attached is specified as data including the search keyword.

CITATION LIST

Non-Patent Literature

Non-Patent Literature 1: Boneh, Di Crescenzo, Ostrovski, and Persiano, "Public key encryption with keyword search" EUROCRYPT 2004, pp 506-522
Non-Patent Literature 2: Allison Lewko, Tatsuaki Okamoto, Amit Sahai, Katsuyuki Takashima, Brent Waters, "Fully Secure Functional Encryption: Attribute-Based Encryption and (Hierarchical) Inner Product Encryption", EUROCRYPT2010, Lecture Notes In Computer Science, 2010, Volume 6110/2010.

SUMMARY OF INVENTION

Technical Problem

Conventionally, in case of searching encrypted genetic information, the genetic information is temporarily decrypted and searched when the search is conducted.

Even if the searchable encryption scheme is used, the search index which is generated by plaintext data is appended to the encrypted genetic information, and the search is conducted using the search index. Further, a huge amount of search indexes are appended to one piece of genetic information, which requires a huge amount of time for searching the information.

Accordingly, a privileged user of the computer that stores the genetic information is able to freely access the data during decrypted or the search index. Therefore, it is impossible to say that the genetic information is completely concealed to the third party.

The present invention aims to search the genetic information while keeping the genetic information completely concealed to the third party.

Solution to Problem

According to the present invention, a genetic information storage apparatus makes a storage apparatus store genetic information, the genetic information storage apparatus includes:
a reference gene obtainment part to obtain a reference gene which is predefined genetic information;
a gene input part to receive a target gene which is the genetic information to be stored in the storage apparatus;
a difference generation part to compare the reference gene obtained by the reference gene obtainment part with the target gene received by the gene input part to generate differential information;
a data encryption part to encrypt the target gene to generate an encrypted gene;
an encrypted tag generation part to generate an encrypted tag in which the differential information generated by the difference generation part is embedded; and
a data storage part to make the storage apparatus store the encrypted gene generated by the data encryption part with related to the encrypted tag generated by the encrypted tag generation part.

The differential information includes information of a plurality of types,
the genetic information storage apparatus further includes:
a differential information substitution part to divide possible values of predefined types included in the differential information into a plurality of blocks, and substitutes a value of the type in the differential information generated by the difference generation part with identifying information identifying a block to which the value belongs, and
the encrypted tag generation part encrypts the differential information substituted by the differential information substitution part to generate the encrypted tag.

The differential information substitution part divides the possible values of the types into a plurality of blocks so that a part of the values belonging to each block should also belong to another block, and substitutes the value of the types in the differential information generated by the differential information generation part with the identifying information identifying each block to which the value belongs to.

The encrypted tag generation part sets, when a cipher attribute set in encrypted data does not correspond to a key attribute set in a private key, based on an encryption scheme according to which the encrypted data is not decrypted by the private key, attribute information of a user who is allowed to search the encrypted gene and the differential information as the cipher attribute, and encrypts a random number value, to generate the encrypted tag.

The genetic information storage apparatus sets, based on the encryption scheme, attribute information of a user who is allowed to decrypt the encrypted gene as the cipher attribute, and encrypts the target gene, to generate the encrypted gene.

According to the present invention, a genetic information search apparatus searches genetic information stored in a storage apparatus managed by a data management apparatus, the genetic information search apparatus includes:

a differential information input part to receive differential information of the genetic information to be searched with a reference gene which is predefined genetic information;

a search query generation part to generate a search query in which the differential information received by the differential information input part is embedded; and a genetic information obtainment part to send the search query generated by the search query generation part to the data management apparatus, and obtains the genetic information including the differential information.

The differential information includes information of a plurality of types, the genetic information search apparatus further includes:

a differential information substitution part to divide possible values of predefined types included in the differential information into a plurality of blocks, and substitutes a value of the type in the differential information with identifying information identifying a block to which the value belongs, and the search query generation part generates a search query in which the differential information substituted by the differential information substitution part is embedded.

The differential information substitution part divides the possible values of predefined types into a plurality of blocks so that a part of the values belonging to each block is made to belong to another block, and substitutes the value of the types in the differential information with identifying information identifying each block to which the value belongs.

The genetic information search apparatus further comprises:

a user private key management part to manage, when a cipher attribute set in encrypted data does not correspond to a key attribute set in a private key, a private key of an encryption scheme according to which the encrypted data is not able to be decrypted by the private key, the private key in which attribute information of a user being set as the key attribute, and the search query generation part adds the differential information as a key attribute of the private key managed by the user private key management part, to generate the search query.

The genetic information obtainment part sets, according to the encryption scheme, attribute information of a user who is allowed to decrypt as the cipher attribute, obtains encrypted gene which is the encrypted genetic information as genetic information including the differential information, and the genetic information search apparatus further includes:

a decryption part to decrypt the encrypted gene using the private key managed by the user private key management part.

According to the present invention, a genetic information storage program makes a storage apparatus store genetic information, the genetic information storage program which causes a computer to execute:

a reference gene obtainment process to obtain a reference gene which is predefined genetic information;

a gene input process to receive a target gene which is the genetic information to be stored in the storage apparatus;

a difference generation process to compare the reference gene obtained by the reference gene obtainment process with the target gene received by the gene input process to generate differential information;

a data encryption process to encrypt the target gene to generate an encrypted gene;

an encrypted tag generation process to generate an encrypted tag in which the differential information generated by the difference generation process is embedded; and a data storage process to make the storage apparatus store the encrypted gene generated by the data encryption process with related to the encrypted tag generated by the encrypted tag generation process.

The differential information includes information a plurality of types, the genetic information storage program further causes the computer to execute:

a differential information substitution process to divide possible values of predefined types included in the differential information into a plurality of blocks, and substitutes a value of the type in the differential information generated by the difference generation process with identifying information identifying a block to which the value belongs, and the encrypted tag generation process encrypts the differential information substituted by the substitution process to generate an encrypted tag.

The differential information substitution process divides the possible values of the types into a plurality of blocks so that a part of the values belonging to each block should also belong to another block, and substitutes the value of the types in the differential information generated by the differential information generation process with the identifying information identifying each block to which the value belongs to.

The encrypted tag generation process sets, when a cipher attribute set in encrypted data does not correspond to a key attribute set in a private key, based on an encryption scheme according to which the encrypted data is not decrypted by the private key, attribute information of a user who is allowed to search the encrypted gene and the differential information as the cipher attribute, and encrypts a random number value, to generate the encrypted tag.

The genetic information storage program sets, based on the encryption scheme, attribute information of a user who is allowed to decrypt the encrypted gene as the cipher attribute, and encrypts the target gene, to generate the encrypted gene.

According to the present invention, a genetic information search program searches genetic information stored in a storage apparatus managed by a data management apparatus, the genetic information search program which causes a computer to execute:

a differential information input process to receive differential information of the genetic information to be searched with a reference gene which is predefined genetic information;

a search query generation process to generate a search query in which the differential information received by the differential information input process is embedded; and a genetic information obtainment process to send the search query generated by the search query generation process to the data management apparatus, and obtains the genetic information including the differential information.

The differential information includes a plurality of types of information, the genetic information search program further includes:

a differential information substitution process to divide possible values of predefined types included in the differential information into a plurality of blocks, and substitutes a value of the type in the differential information with identifying information identifying a block to which the value belongs, and the search query generation process generates a search query in which the differential information substituted by the differential information substitution process is embedded.

The differential information substitution process divides the possible values of predefined types into a plurality of blocks so that a part of the values belonging to each block is made to belong to another block, and substitutes the value of the types in the differential information with identifying information identifying each block to which the value belongs.

The genetic information search program further causes the computer to execute:

a user private key management process to manage, when a cipher attribute set in encrypted data does not correspond to a key attribute set in a private key, a private key of an encryption scheme according to which the encrypted data is not able to be decrypted by the private key, the private key in which attribute information of a user being set as the key attribute, and the search query generation process adds the differential information as a key attribute of the private key managed by the user private key management process, to generate the search query.

The genetic information obtainment process sets, according to the encryption scheme, attribute information of a user who is allowed to decrypt as the cipher attribute, obtains encrypted gene which is the encrypted genetic information as genetic information including the differential information, and the genetic information search program further causes the computer to execute:

a decryption process to decrypt the encrypted gene using the private key managed by the user private key management process.

According to the present invention, a genetic information storage method makes a storage apparatus store genetic information, the genetic information storage method includes:

a reference gene obtainment step to obtain a reference gene which is predefined genetic information;

a gene input step to receive a target gene which is the genetic information to be stored in the storage apparatus;

a difference generation step to compare the reference gene obtained by the reference gene obtainment step with the target gene received by the gene input step to generate differential information;

a data encryption step to encrypt the target gene to generate an encrypted gene;

an encrypted tag generation step to generate an encrypted tag in which the differential information generated by the difference generation step is embedded; and a data storage step to make the storage apparatus store the encrypted gene generated by the data encryption step with related to the encrypted tag generated by the encrypted tag generation step.

According to the present invention, a genetic information search method searches genetic information stored in a storage apparatus managed by a data management apparatus, the genetic information search method includes:

a differential information input step to receive differential information of the genetic information to be searched with a reference gene which is predefined genetic information;

a search query generation step to generate a search query in which the differential information received by the differential information input step is embedded; and a genetic information obtainment step to send the search query generated by the search query generation step to the data management apparatus, and obtains the genetic information including the differential information.

According to the present invention, a genetic information search system having a genetic information storage apparatus which makes a storage apparatus managed by a data management apparatus store genetic information and a genetic information search apparatus which searches genetic information including a search keyword from the genetic information that is made to store by the genetic information storage apparatus, the genetic information storage apparatus includes:

a reference gene obtainment part to obtain a reference gene which is predefined genetic information;

a gene input part to receive a target gene which is the genetic information to be stored in the storage apparatus;

a difference generation part to compare the reference gene obtained by the reference gene obtainment part with the target gene received by the gene input part and to generate differential information;

a data encryption part to encrypt the target gene to generate an encrypted gene;

an encrypted tag generation part to generate an encrypted tag in which the differential information generated by the difference generation part is embedded; and a data storage part to make the storage apparatus store the encrypted gene generated by the data encryption part with related to the encrypted tag generated by the encrypted tag generation part, and the genetic information search apparatus includes:

a differential information input part to receive differential information of the genetic information to be searched with a reference gene which is predefined genetic information;

a search query generation part to generate a search query in which the differential information received by the differential information input part is embedded; and a genetic information obtainment part to send the search query generated by the search query generation part to the data management apparatus, and obtains the genetic information including the differential information.

Advantageous Effects of Invention

According to the present invention, while genetic information stored in the database and a tag which is a search index, and genetic information which is used for a search keyword are kept encrypted, the genetic information including the search keyword can be extracted from the database. Accordingly, the genetic information is completely concealed to the third party.

In particular, according to the present invention, differential information from reference gene is set to the search index and the search keyword. Therefore, the number of search indexes can be small, which enables to conduct search at a high speed.

BRIEF DESCRIPTION OF DRAWINGS

FIG. 17 is an explanatory diagram of user ID information database.
FIG. 21 illustrates a storage example of the encrypted data.
FIG. 24 is an explanatory diagram of an access authority management table.

DESCRIPTION OF EMBODIMENTS

Embodiment 1

Figure 1:
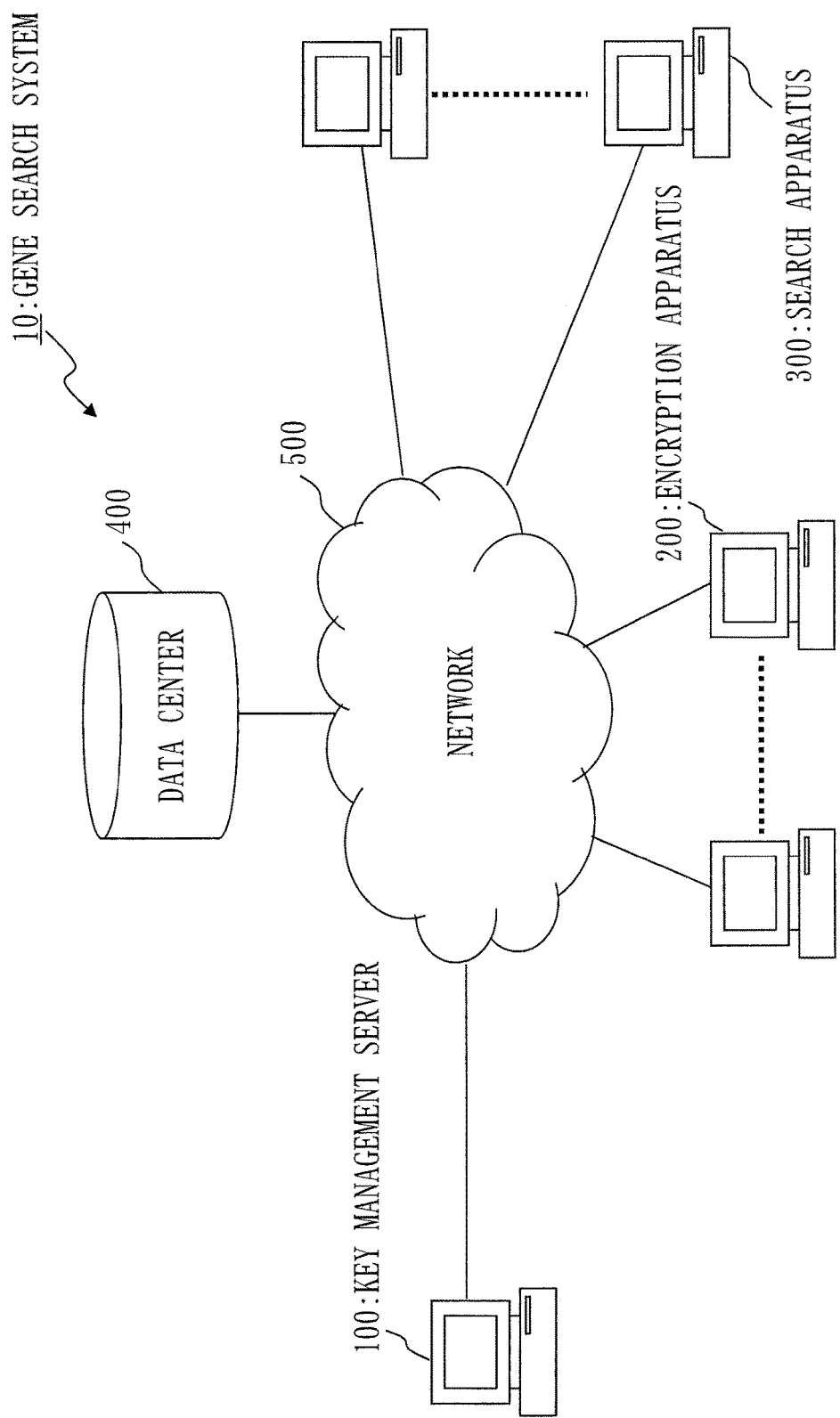
FIG. 1 is a configuration diagram of a gene search system 10.

FIG. 1 is a configuration diagram of a gene search system 10.

The gene search system 10 is provided with a key management server 100, a plurality of encryption apparatuses 200, a plurality of search apparatuses 300, and a data center 400 (a data management apparatus). The key management server 100, the encryption apparatuses 200, the search apparatuses 300, and the data center 400 are connected via a network 500.

The key management server 100 is a server which generates a user private key such as a user private key for encryption and a user private key for searchable encryption to distribute to the encryption apparatus 200 and the search apparatus 300. Here, the user private key for encryption is a key used for decrypting encrypted data, and the user private key for the searchable encryption is a key used for the searchable encryption.

The encryption apparatus 200 is a terminal to encrypt information to be stored in the data center 400. The encryption apparatus 200 is a terminal which is used by, mainly, users such as doctors of the hospital, employees of the genome decoding center, or patients.

The search apparatus 300 is a terminal which is used for searching and obtaining information stored in the data center 400. The search apparatus 300 is used by, mainly, users such as researchers of the pharmaceutical companies and the like or doctors of the hospital.

The data center 400 is a server which stores genome information collected from the patients and electronic health record in which medical history of the patients is described and the like. The data center 400 provides service to search or browse, in response to request from the user such as patients, doctors, researchers, and the like, the genome information, the electronic health record and the like.

The network 500 is a public network, for instance, the Internet.

Figure 2:
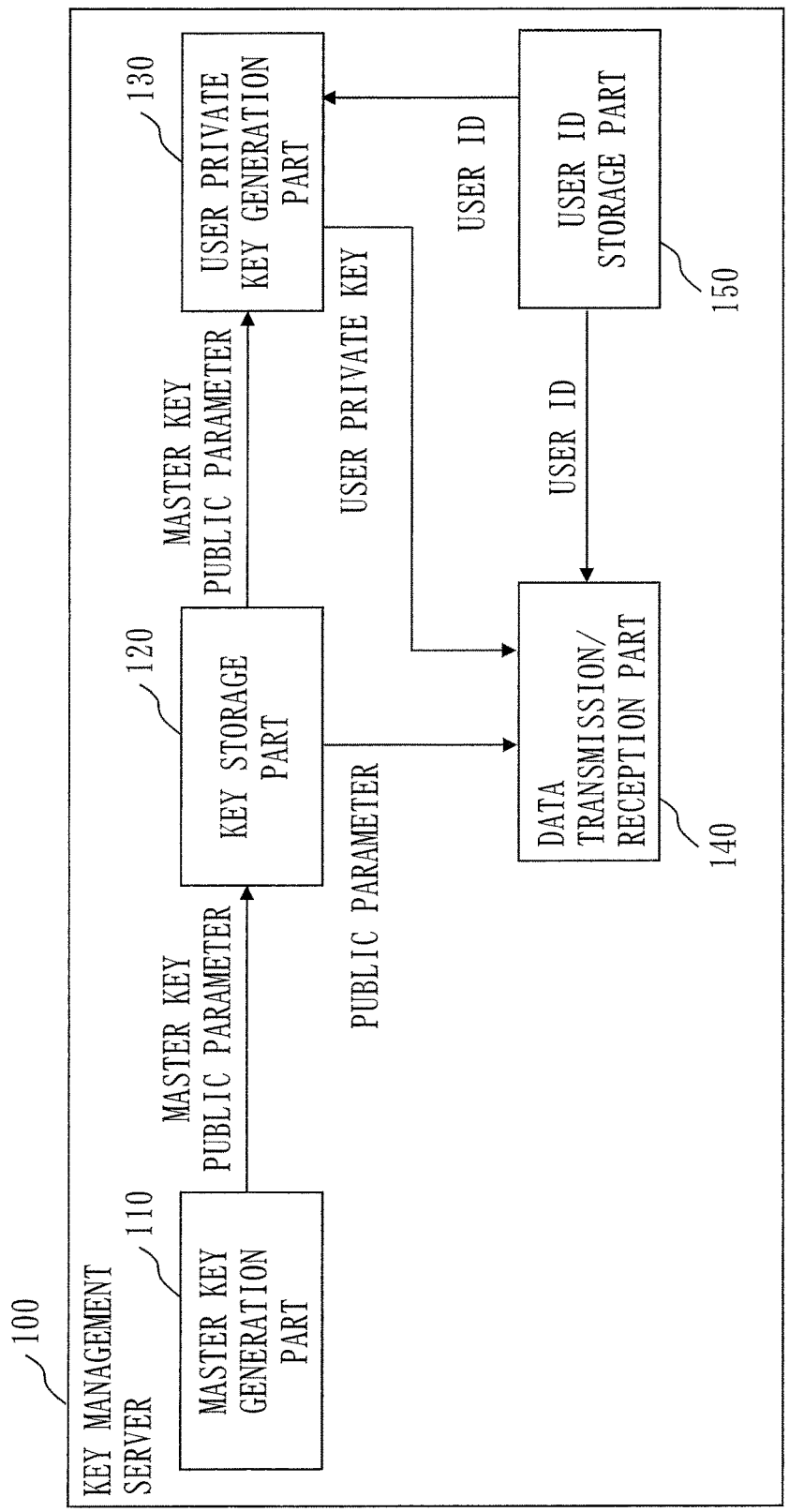
FIG. 2 is a configuration diagram of a key management server 100.

FIG. 2 is a configuration diagram of the key management server 100.

The key management server 100 is provided with a master key generation part 110, a key storage part 120, a user private key generation part 130, a data transmission/reception part 140, and a user ID storage part 150.

The master key generation part 110 generates, by a processing device, a public parameter to be used by all the users of searchable encryption, and as well generates a master key which will be a base for generating a user private key.

The key storage part 120 stores the master key and the public parameter generated by the master key generation part 110.

The user private key generation part 130 generates, by the processing device, using a user ID assigned to the users uniquely, the user private key from the master key.

The data transmission/reception part 140 sends the public parameter to the encryption apparatus 200, the search apparatus 300, and the data center 400 via the network 500. Further, the data transmission/reception part 140 sends the user private key to the search apparatus 300 via the network 500. Further, the data transmission/reception part 140 sends, in response to the request from the user, the user ID to the users of the encryption apparatus 200, the search apparatus 300, and the data center 400.

The user ID storage part 150 stores the user ID of each user in a storage apparatus. The user ID is the attribute information such as a name of the user, affiliation, a login ID, a mail address. The user ID storage part 150 may store not only the attribute information at present but also the attribute information in the past as a history.

Figure 3:
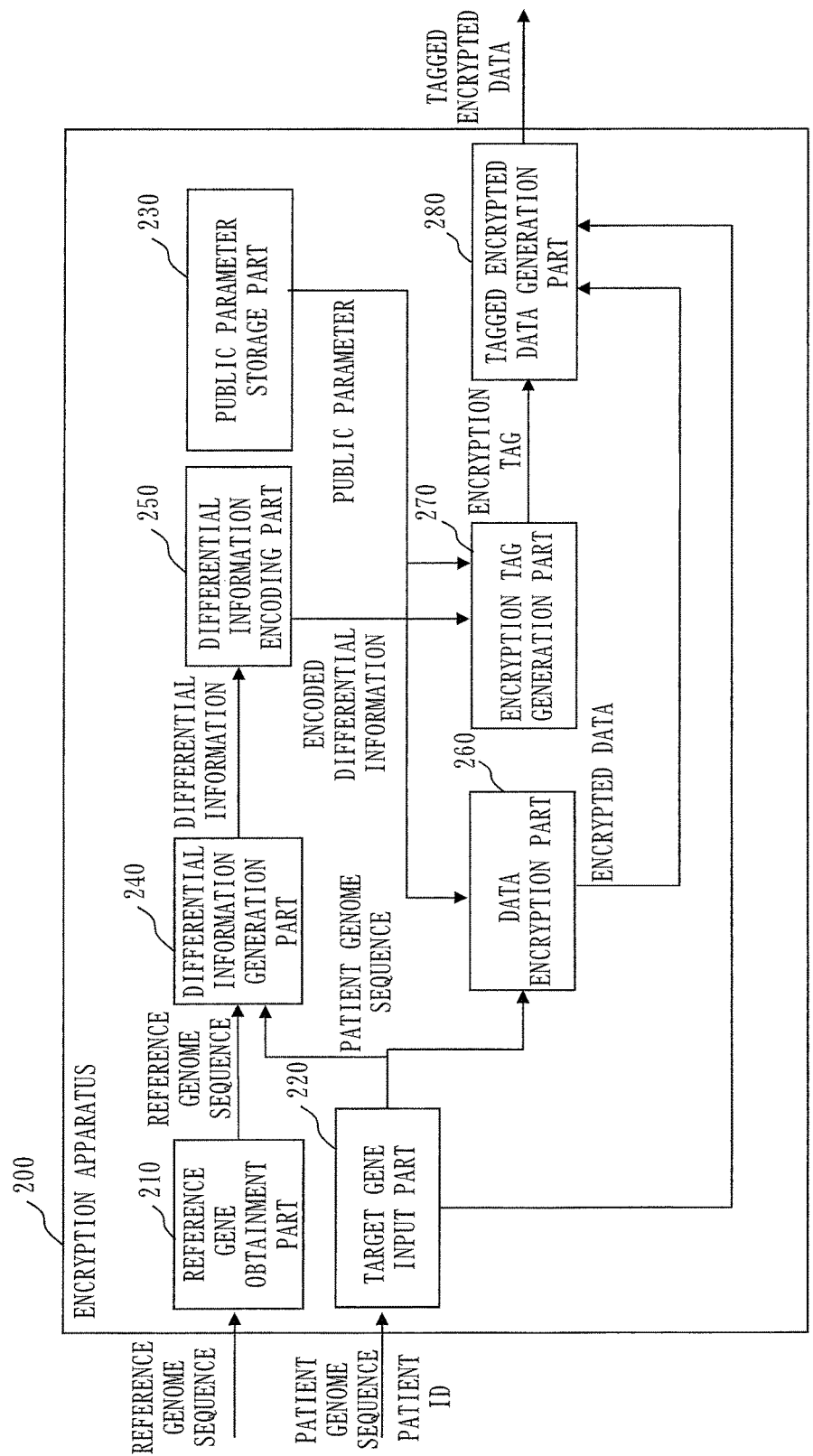
FIG. 3 is a configuration diagram of an encryption apparatus 200.

FIG. 3 is a configuration diagram of the encryption apparatus 200.

The encryption apparatus 200 is provided with a reference gene obtainment part 210, a target gene input part 220, a public parameter storage part 230, a differential information generation part 240, a differential information encoding part 250, a data encryption part 260, an encrypted tag generation part 270, and a tagged encrypted data generation part 280.

The reference gene obtainment part 210 obtains a predefined genome sequence which is laid open to public as reference genome sequence (reference gene).

The target gene input part 220 obtains a patient genome sequence (target gene) to be stored in the data center 400. Further, the target gene input part 220 also obtains, together with the patient genome sequence, a patient ID indicating a patient of the patient genome sequence.

The public parameter storage part 230 receives a public parameter generated by the key management server 100 and stores the public parameter in the storage apparatus.

The differential information generation part 240 compares, by the processing device, the patient genome sequence with the reference genome sequence, and generates a plurality pieces of differential information.

The differential information encoding part 250 encodes, by the processing device, each piece of differential information generated by the differential information generation part 240 into a form suitable to the encryption search, to generate encoded differential information. The form suitable to the encryption search will be discussed later.

The data encryption part 260 encrypts, by the processing device, the patient genome sequence received by the target gene input part 220, to generate encrypted data (encrypted gene).

The encrypted tag generation part 270 encrypts, by the processing device, the encoded differential information generated by the differential information encoding part 250, to generate an encrypted tag.

The tagged encrypted data generation part 280 combines, by the processing device, the encrypted data generated by the data encryption part 260, a plurality of encrypted tags generated by the encrypted tag generation part 270, and the patient ID, to generate tagged encrypted data. The tagged encrypted data generation part 280 requests the data center 400 to store the generated tagged encrypted data.

Figure 4:
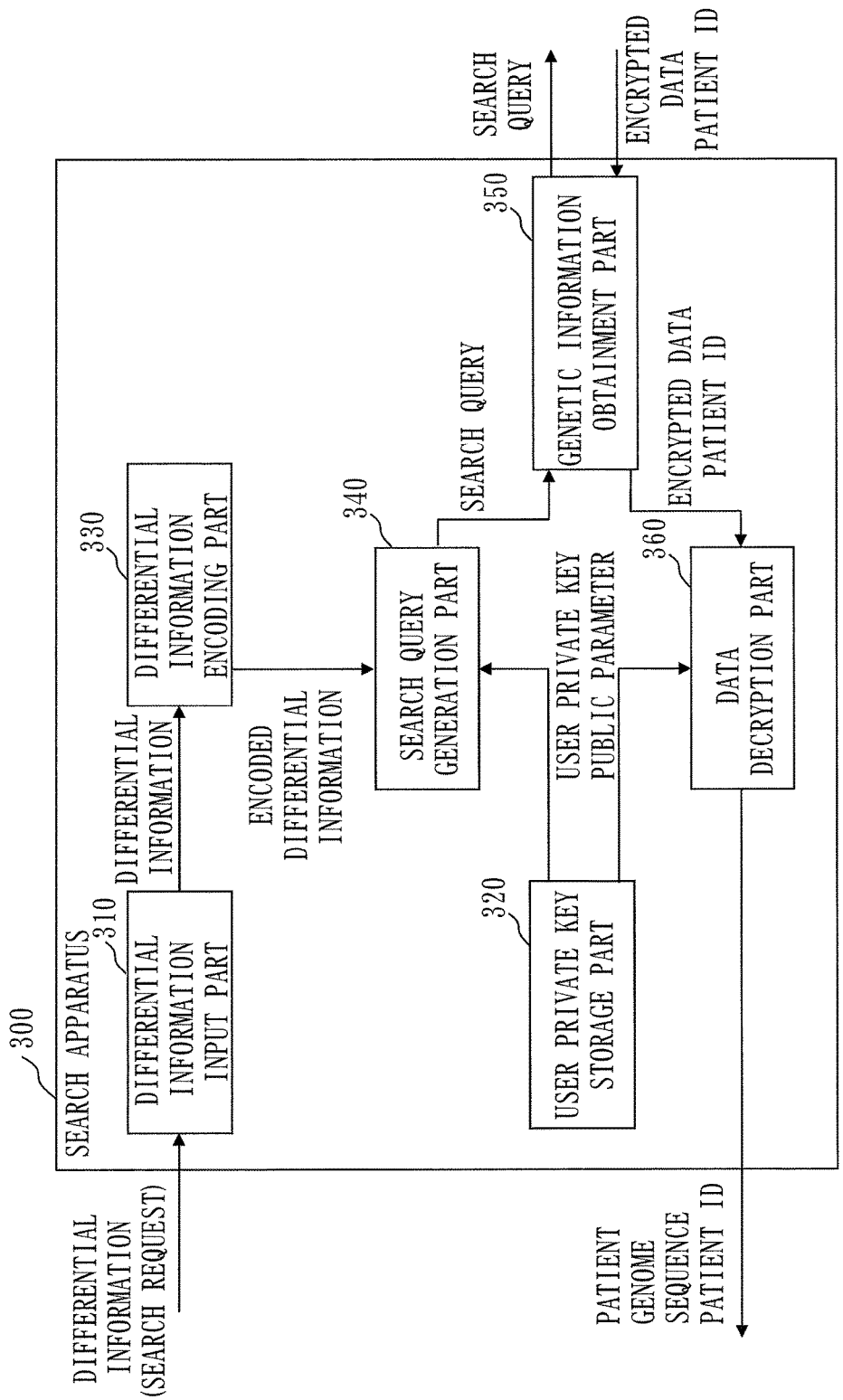
FIG. 4 is a configuration diagram of a search apparatus 300.

FIG. 4 is a configuration diagram of the search apparatus 300.

The search apparatus 300 is provided with a differential information input part 310, a user private key storage part 320, a differential information encoding part 330, a search query generation part 340, a genetic information obtainment part 350, and a data decryption part 360.

The differential information input part 310 receives, by the inputting device, a search request including the differential information with the reference genome sequence as a search keyword.

The user private key storage part 320 stores a user private key issued for each user by the key management server 100 and the public parameter in the storage apparatus.

The differential information encoding part 330 has a function being the same as the differential information encoding part 250. The differential information encoding part 330 encodes, by the processing device, the differential information included in the search request received by the differential information input part 310 into a form suitable to the encryption search, to generate encoded differential information.

The search query generation part 340 generates, by the processing device, a search query using the user private key and the public parameter stored by the user private key storage part 320 and the encoded differential information generated by the differential information encoding part 330.

The genetic information obtainment part 350 sends the search query generated by the search query generation part 340 to the data center 400 via the network 500. Then, the genetic information obtainment part 350 receives the encrypted data which is encrypted patient genome sequence including the differential information included in the search request (or including similar differential information) from the data center 400 via the network 500. Further, the genetic information obtainment part 350 receives the patient ID together with the encrypted data.

The data decryption part 360 decrypts, by the processing device, the encrypted data received from the data center 400 using the user private key stored by the user private key storage part 320, and obtains a patient genome sequence.

Figure 5:
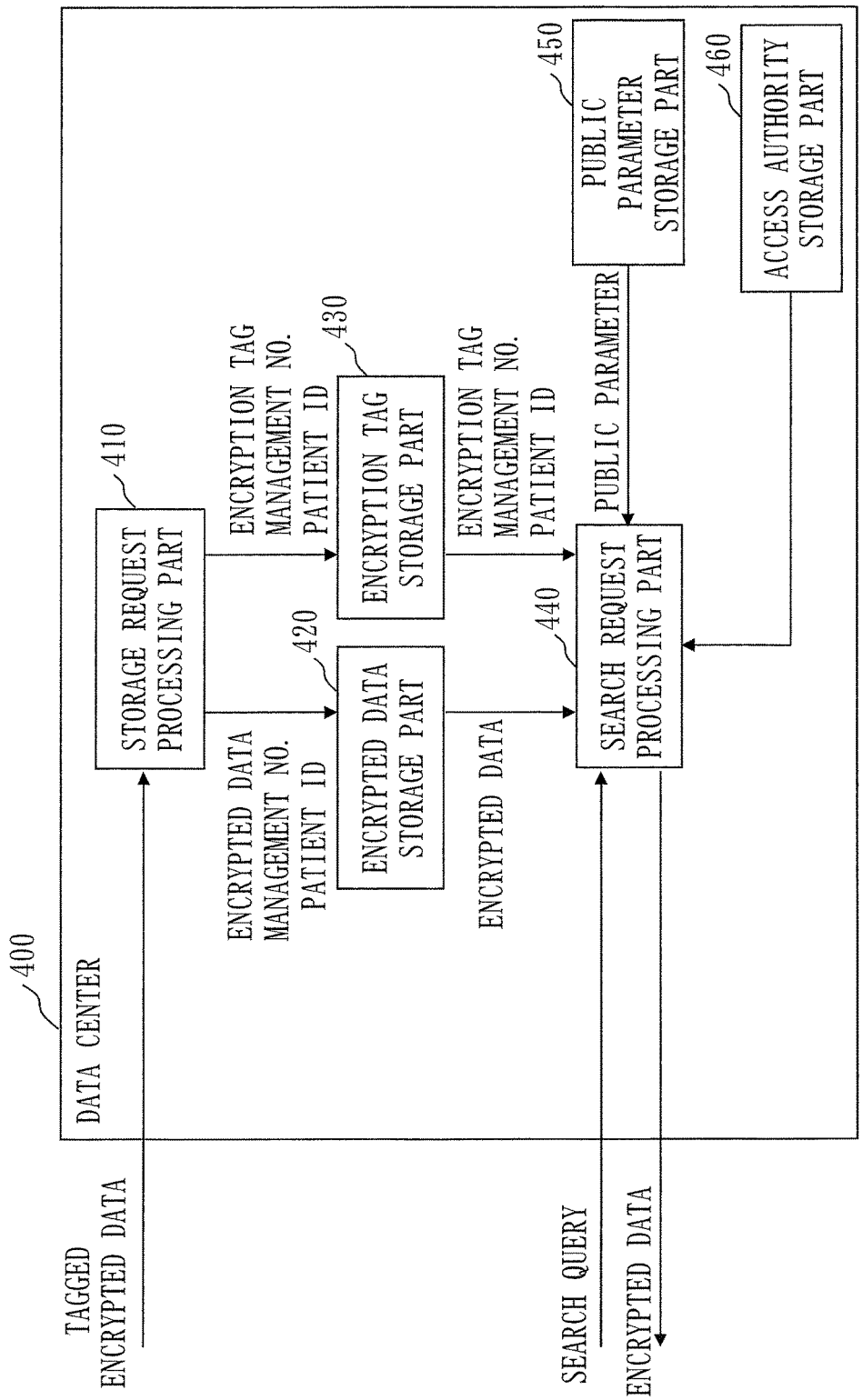
FIG. 5 is a configuration diagram of a data center 400.

FIG. 5 is a configuration diagram of the data center 400.

The data center 400 is provided with a storage request processing part 410, an encrypted data storage part 420, an encrypted tag storage part 430, a search request processing part 440, a public parameter storage part 450, and an access authority storage part 460.

The storage request processing part 410 receives the tagged encrypted data from the encryption apparatus 200. The storage request processing part 410 analyzes the received tagged encrypted data, and decomposes into the encrypted data, a plurality of encrypted tags and a patient ID. The storage request processing part 410 assigns a common management number to the encrypted data and each of the encrypted tags which have been decomposed. The storage request processing part 410 sends the encrypted data together with the patient ID and the management number to the encrypted data storage part 420, and sends each of the encrypted tags together with the patient ID and the management number to the encrypted tag storage part 430.

The encrypted data storage part 420 stores the encrypted data received from the storage request processing part 410 with related to the patient ID and the management number in the storage apparatus.

The encrypted tag storage part 430 stores the encrypted tag received from the storage request processing part 410 with related to the patient ID and the management number in the storage apparatus.

The search request processing part 440 receives a search query from the search apparatus 300. The search request processing part 440 carries out, by the processing device, a comparison process of the received search query with the encrypted tag. By this comparison process, it is determined the differential information of the patient genome sequence included in the encrypted tag matches a condition specified by the differential information (search request) of the patient genome sequence included in the search query. Then, the search request processing part 440 obtains the encrypted data related to the encrypted tag which has been hit by the search from the encrypted data storage part 420, and returns the encrypted data to the search apparatus 300. Here, the encrypted data related to the encrypted tag is the encrypted data to which the management number being the same as the encrypted tag is assigned.

The public parameter storage part 450 receives the public parameter generated by the key management server 100, and stores the public parameter in the storage apparatus.

The access authority storage part 460 manages persons to whom the patient allows to disclose the patient genome sequence.

The encryption scheme used by the gene search system 10 will be explained.

The gene search system 10 uses the encryption scheme so-called hierarchical predicate encryption for inner products described in Non-Patent Literature 2 and the like, and the searchable encryption scheme similarly using the hierarchical predicate encryption for inner products, according to which a keyword is searchable in an encrypted status.

Figure 6:
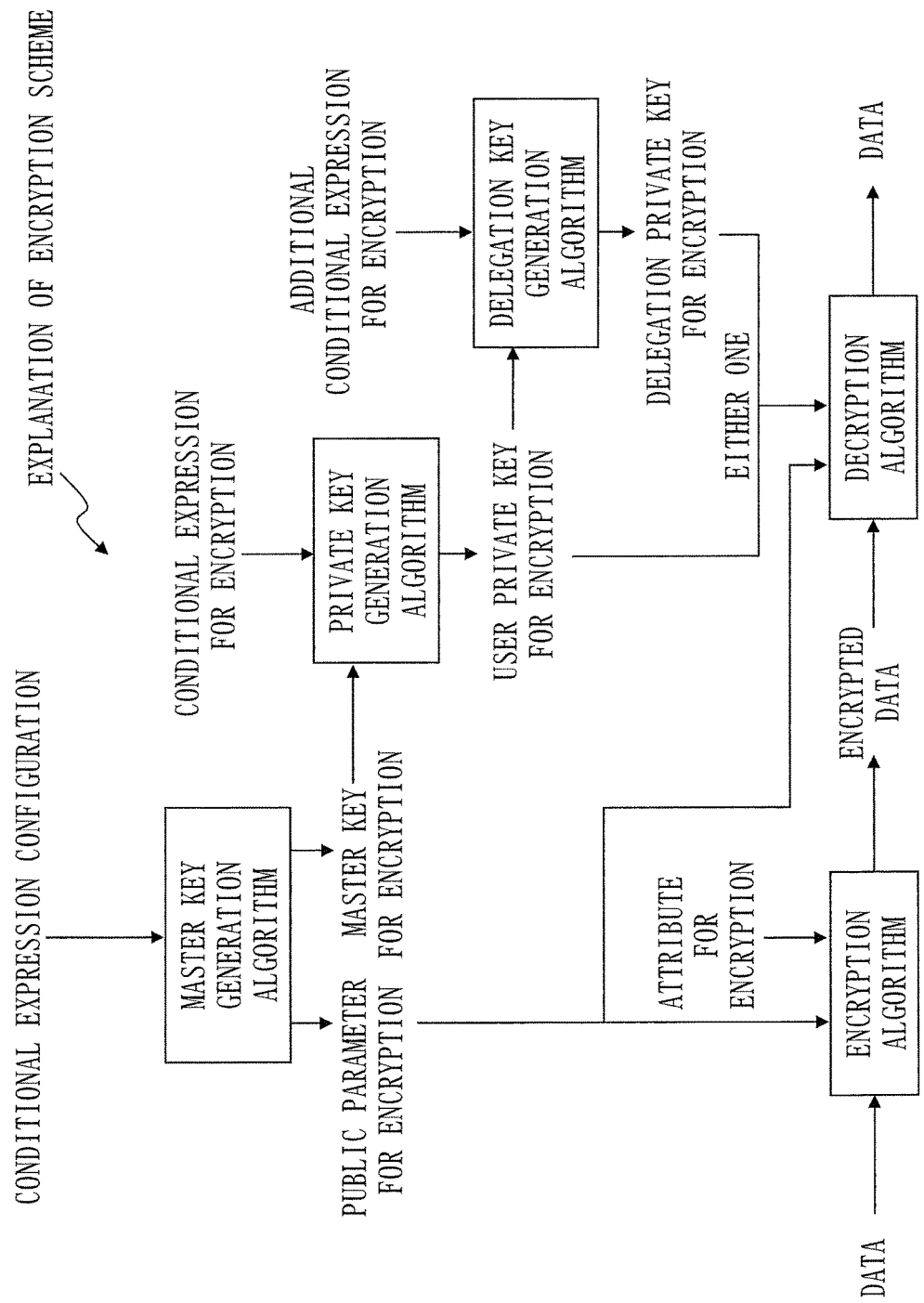
FIG. 6 is an explanatory diagram of an encryption scheme using hierarchical predicate encryption for inner products.

FIG. 6 is an explanatory diagram of the encryption scheme using the hierarchical predicate encryption for inner products.

The encryption scheme is configured by a master key generation algorithm, a private key generation algorithm, a delegation key generation algorithm, an encryption algorithm, and a decryption algorithm.

At first, a master key for encryption and a public parameter for encryption are generated using the master key generation algorithm. The master key for encryption is a private key used for generating a user private key for encryption of the decrypting user. The public parameter for encryption is open information to be used for encryption and is broadly distributed to the users who carry out encryption.

Note, in case of this process, it is necessary to decide a configuration of a conditional expression previously, and to supply the conditional expression as a parameter. The existing documents of the hierarchical predicate encryption for inner products such as Non-Patent Literature 2 and the like describe that the configuration of the conditional expression is not given, but the number of degrees in case of expressing the conditional expression as a vector should be given. In the view of facilitating the understanding, it is assumed that the conditional expression is given here. Hereinafter, the same can be applied.

Next, using the private key generation algorithm, the user private key for encryption to be distributed to the decrypting user is issued from the conditional expression for encryption. The conditional expression for encryption describes a condition according to which what kind of attribute is included in the document that can be decrypted by the decrypting user is decided as a conditional expression using a logical operation of AND/OR.

Next, the data is encrypted using the encryption algorithm. At this time, the attribute for encryption to be appended to the encrypted data is specified and embedded in the encrypted data.

Finally, the encrypted data is decrypted using the decryption algorithm. At the time of decryption, the user private key for encryption is specified; only the encrypted data to which the attribute for encryption which satisfies the conditional expression embedded in the user private key for encryption is appended. No encrypted data which does not satisfy the conditional expression can be decrypted.

Here, the hierarchical predicate encryption for inner products also includes a feature of key delegation. This is, on generating the user private key for encryption, only a part of the conditional expression is set, and a part of the conditional expression remains unset. The key delegation is a function to set a conditional expression additionally to the unset conditional expression.

Specifically, using the delegation key generation algorithm, the additional conditional expression for encryption which is to be set additionally with respect to the user private key for encryption is specified, and the delegation private key for encryption is generated. This delegation private key for encryption can be used for decrypting the encrypted data similarly to the user private key for encryption.

In a slightly different way of speaking, according to the private key generation algorithm, the user private key for encryption in which the attribute information of the decrypting user is set as the key attribute is issued. Further, according to the encryption algorithm, the encrypted data in which the attribute information of the user being able to decrypt is set as the cipher attribute is generated. Then, according to the decryption algorithm, only when the key attribute set in the user private key for encryption is related to the cipher attribute set in the encrypted data, the encrypted data can be decrypted by the user private key for encryption.

Further, according to the delegation key generation algorithm, the attribute information is additionally set in the user private key for encryption, a lower user private key for encryption being able to decrypt only a part of the encrypted data using the user private key for encryption is generated.

Figure 7:
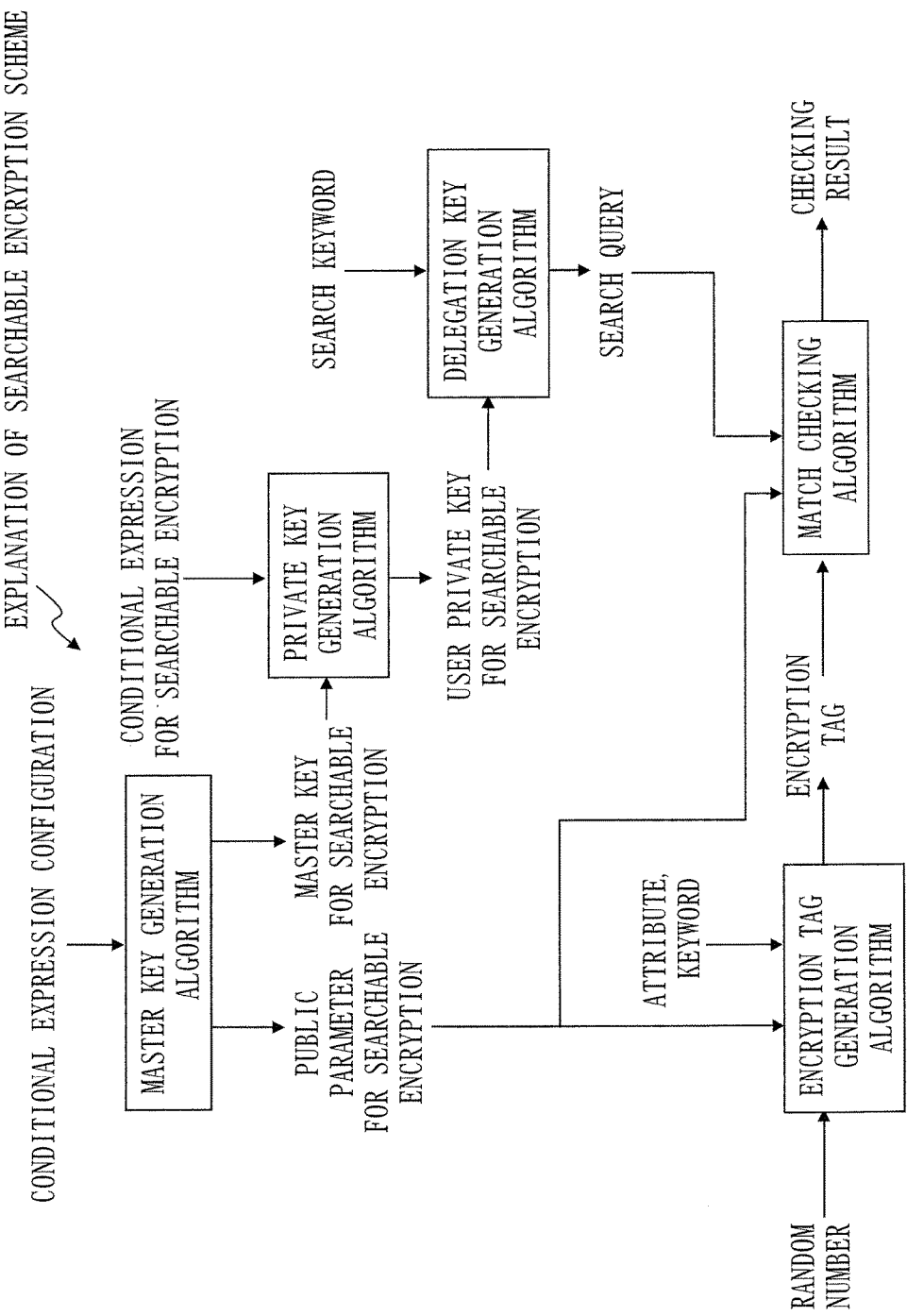
FIG. 7 is an explanatory diagram of a searchable encryption scheme using the hierarchical predicate encryption for inner products.

FIG. 7 is an explanatory diagram of the searchable encryption scheme using the hierarchical predicate encryption for inner products.

The searchable encryption scheme is configured by a master key generation algorithm, a private key generation algorithm, a delegation key generation algorithm, an encrypted tag generation algorithm, and a match checking algorithm.

At first, using the master key generation algorithm, a master key for the searchable encryption and a public parameter for the searchable encryption are generated. The master key for the searchable encryption is a private key used for generating a user private key for the searchable encryption of the searching user. The public parameter for the searchable encryption is open information used for searching, which is broadly distributed to searching users.

Here, the description of the conditional expression is the same as the encryption scheme.

Next, using the private key generation algorithm, the user private key for the searchable encryption to be distributed to the searching user is issued from the conditional expression for searchable encryption. The conditional expression for searchable encryption describes a condition according to which what kind of attribute is included in the document which can be searched by the searching user is specified, and in addition, only a frame by which the search keyword is specified by what kind of conditional expression is decided as a conditional expression using a logical operation of AND/OR. The search keyword itself can be set afterwards using the delegation key generation algorithm.

Next, using the encrypted tag generation algorithm, an encrypted tag to be used for the search process is generated. First, an arbitrary random number value is generated, the attribute is decided for limiting the user who is allowed to conduct search, and a keyword is decided. An encrypted tag is generated using the encrypted tag generation algorithm with inputs of the random number value, the attribute, and the keyword. Specifically, the random number value is encrypted using the encryption algorithm, and a combination of the encrypted random number and the random number value is set as an encrypted tag.

Next, a search query is generated using the delegation key generation algorithm. Specifically, a search keyword is embedded in a part, of the user private key for the searchable encryption, whose value remains unspecified to be specified later, and thereby a search query is generated. The search query corresponds to the delegation private key for encryption of the encryption scheme.

Finally, using the match checking algorithm, a match checking is carried out to indicate whether or not the keywords included in both of the search query and the encrypted tag which have been received are the same. Specifically, the encryption random number is taken out from the encrypted tag, and decrypted using the search query corresponding to the delegation private key for encryption. Then, the decrypted result is the same as the random number value included in the encrypted tag, that is, in a case where the decryption is correctly done using the search query, it is determined that the keywords are the same. This is because if the keyword included in the search query (corresponding to the delegation private key for encryption) is not the same as the encryption random number specified at the time of generating the keyword, the random number value cannot be decrypted correctly.

Similarly to the above-discussed encryption scheme, in a slightly different way of speaking, according to the private key generation algorithm, a user private key for the searchable encryption in which the attribute information of the searching user is set as the key attribute is issued. Further, according to the encryption algorithm, the encrypted data in which the attribute information of the user being able to search and the keyword are set as a cipher attribute is generated. According to the delegation key generation algorithm, the search keyword is additionally added to the user private key for the searchable encryption as the key attribute, and a search query is generated.

Then, according to the decryption algorithm, only when the key attribute information set in the search query corresponds to the attribute information set in the encrypted tag, the random number value can be decrypted from the encrypted tag. That is, only when the attribute information of the user set in the search query corresponds to the attribute information of the user set in the encrypted tag, and the search keyword set in the search query corresponds to the keyword set in the encrypted tag, the random number value can be decrypted from the encrypted tag.

The operation of the gene search system 10 will be explained.

The gene search system 10 executes an initialization process, a user private key issuance process, an encryption process, and a search process. Here, the encryption process includes an encryption process of the patient genome sequence and an encryption process of an electronic health record of the patient.

Figure 8:
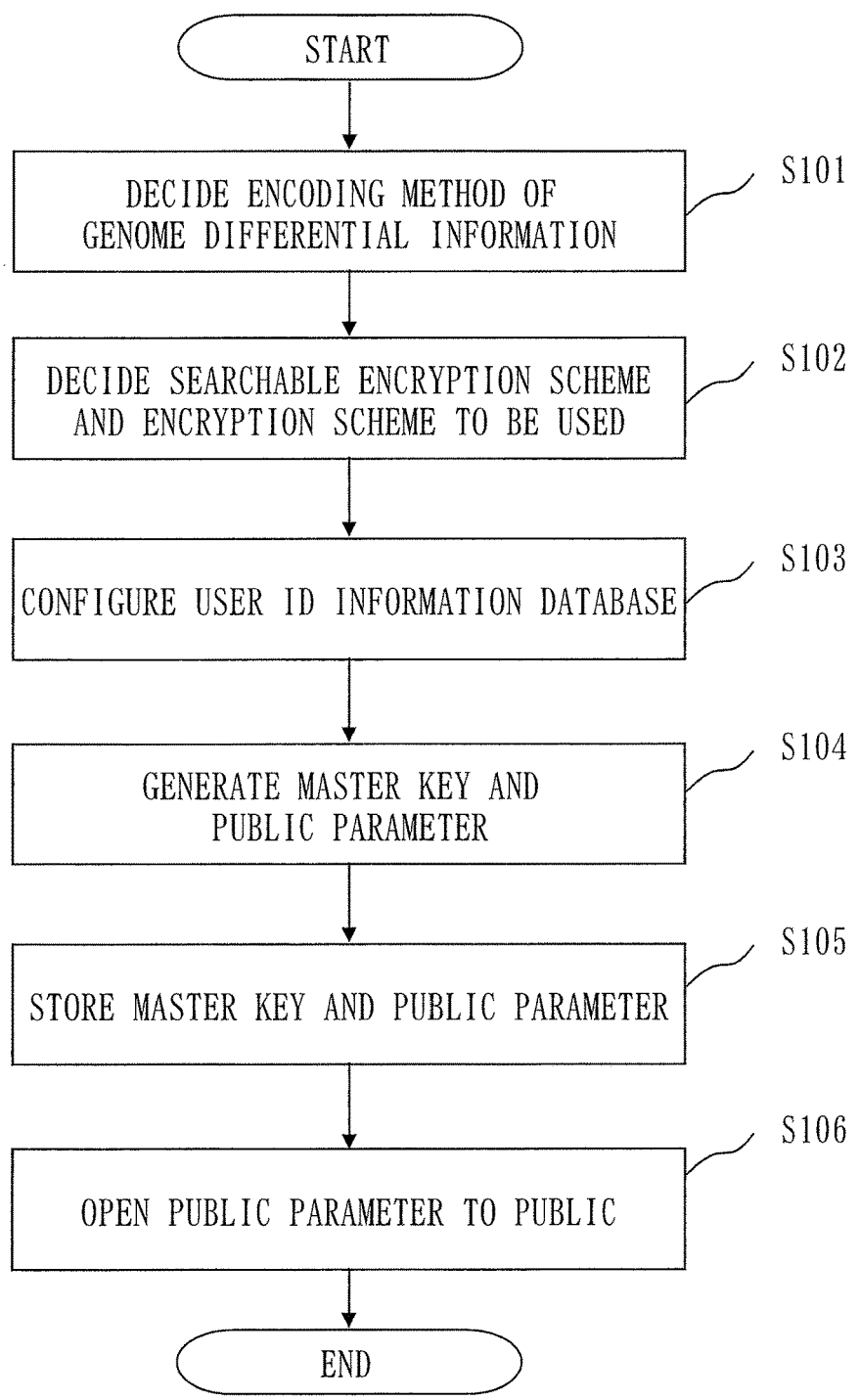
FIG. 8 is a flowchart illustrating a flow of an initialization process.

FIG. 8 is a flowchart illustrating a flow of the initialization process. The initialization process is a process implemented by the key management server 100, and is a process implemented one time before the gene search system 10 is used.

(S101: Encoding Method Determination Process)

The master key generation part 110 decides, by the processing device, a method to encode the differential information of the patient genome sequence. At the time of deciding the encoding method, a search expression which defines how to search is also considered.

The main differential information includes SNV (Single Nucleotide Variant), SV (Structural Variants), or NC (Novel Contig). Then, using the three as examples, the encoding method and the search method will be explained.

Figure 9:
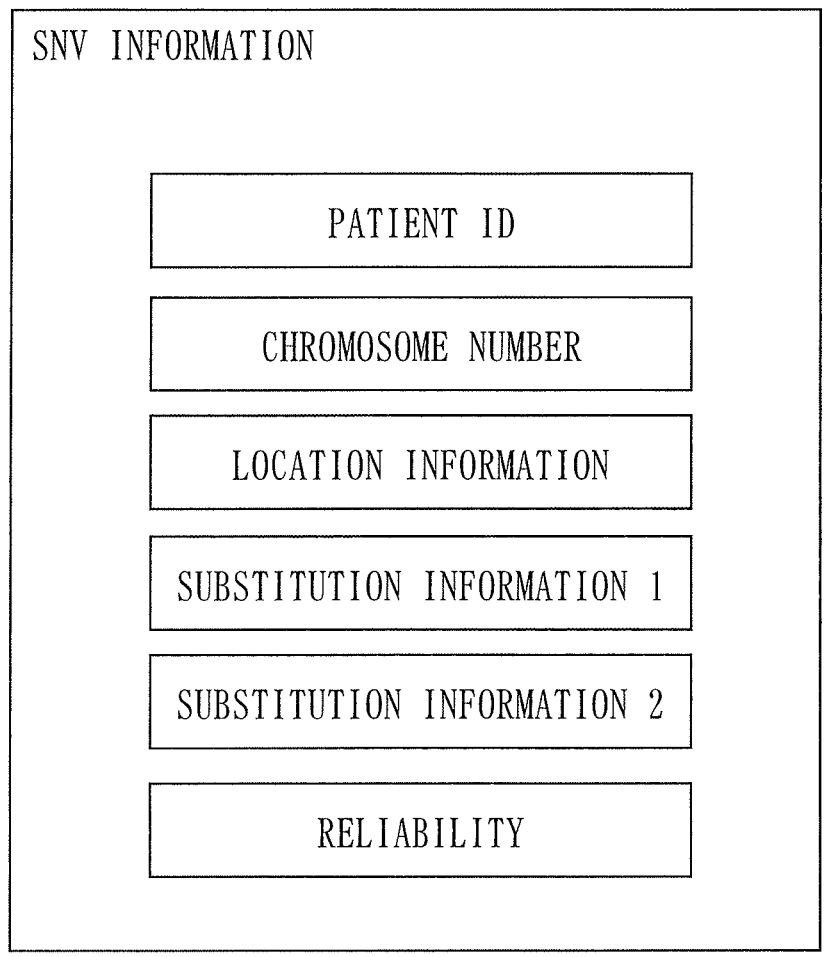
FIG. 9 is a configuration diagram of encoded SNV information.

FIG. 9 is a configuration diagram of the encoded SNV information.

The SNV information indicates that one base is changed in the genome sequence. The SNV information is configured by the patient ID, a chromosome number, location information, substitution information 1, substitution information 2, and reliability.

The patient ID is the identification number assigned to be related to the electronic health record, which is managed separately. Since the patient ID may be a number which can be related to the health record, not only the identification number assigned to the patient by the hospital, but also a random number that is assigned at the time of storing the health record may be set as the patient ID.

The chromosome number indicates the number of chromosome in which SNV is detected. In case of the human genome, for instance, a value such as 1, 2, . . . , 22, X, Y, M, and the like is set.

Figure 10:
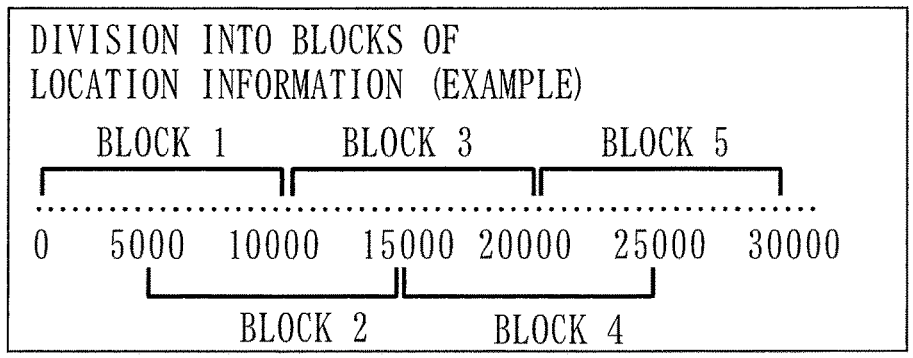
FIG. 10 is an explanatory diagram of dividing into blocks of location information in the SNV information.

The location information is information of location where the SNV is detected. The location is expressed by a numeric value indicating something location of the base sequence; in case of the human genome, it is from 1 to 3 billion. In general, the search for numeric value information such as the location is conducted by specifying a range. However, in the above searchable encryption scheme, since a range search is difficult to be conducted, a range is divided into blocks to accelerate the search. For instance, FIG. 10 illustrates the encoding method for a case in which the range specified at the time of search is suppressed to equal to or less than 5000. In a case where the SNV is detected at the location 7777, it is considered that the block 1 and the block 2 are corresponding locations, and two values of "1" and "2" are set for the location information.

The substitution information 1 and the substitution information 2 are information indicating the change of the genome information. For instance, it is defined to describe "G addition" when the base represented by G is inserted as the SNV, "A deletion" when the base represented by A is erased, and the like, and such values are set. There are two pieces of the substitution information, because in a case where, for instance, the base represented by G is changed to the base represented by A, "G deletion" is indicated for the substitution information 1, and "A addition" and the like is indicated for the substitution information 2.

Figure 11:
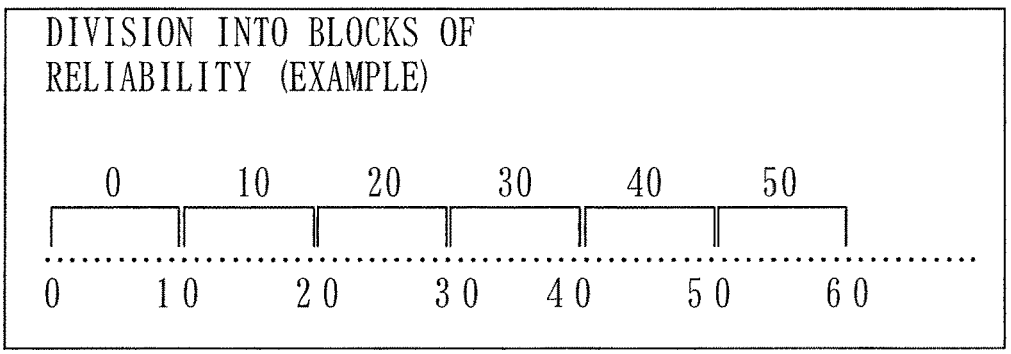
FIG. 11 is an explanatory diagram of dividing into blocks of reliability in the SNV information.

The reliability is information representing the reliability of the SNV information, and is represented by real numbers of 0 through 100. Similarly to the location information, this information is also divided into blocks in order to accelerate the search. For instance, as illustrated in FIG. 11, the reliability is delimited by 10%, and the corresponding values are set. For instance, in a case where the reliability is 7.44%, 0 which is the value of the corresponding block is set.

In case of search, among the above values of the patient ID through the reliability, some values which the user wants to indicate as condition are specified, "*" (wild card) which deems any value as "matched" is indicated for the unspecified location, and the differential information (search request) is generated. Then, a rule is determined, such that with respect to each element of the SNV information, the search is hit when all are matched between the encrypted tag and the search query.

Further, it is also decided under what condition each element matches.

For instance, when the patient ID is specified, if the patient ID is the same, they are deemed as matched. Similarly, as for the chromosome number, when the chromosome number to be searched is specified, if the chromosome number is the same, they are deemed as matched. In case of the location information, for instance, when the range of 7000 to 12000 is to be searched, the block 2 including that range is indicated, and "2" is specified in the search expression. Then, if it is the same as either one of the two values set for the location information of the SNV information, they are deemed as matched. As for the substitution information, the value to be searched is set with the same rule as the value specified for the SNV information, if both are the same, they are deemed as matched. As for the reliability, similarly, when the same values are specified, they are deemed as matched.

As discussed above, the encoding method of the SNV information and a method by which the search is conducted are decided.

Figure 12:
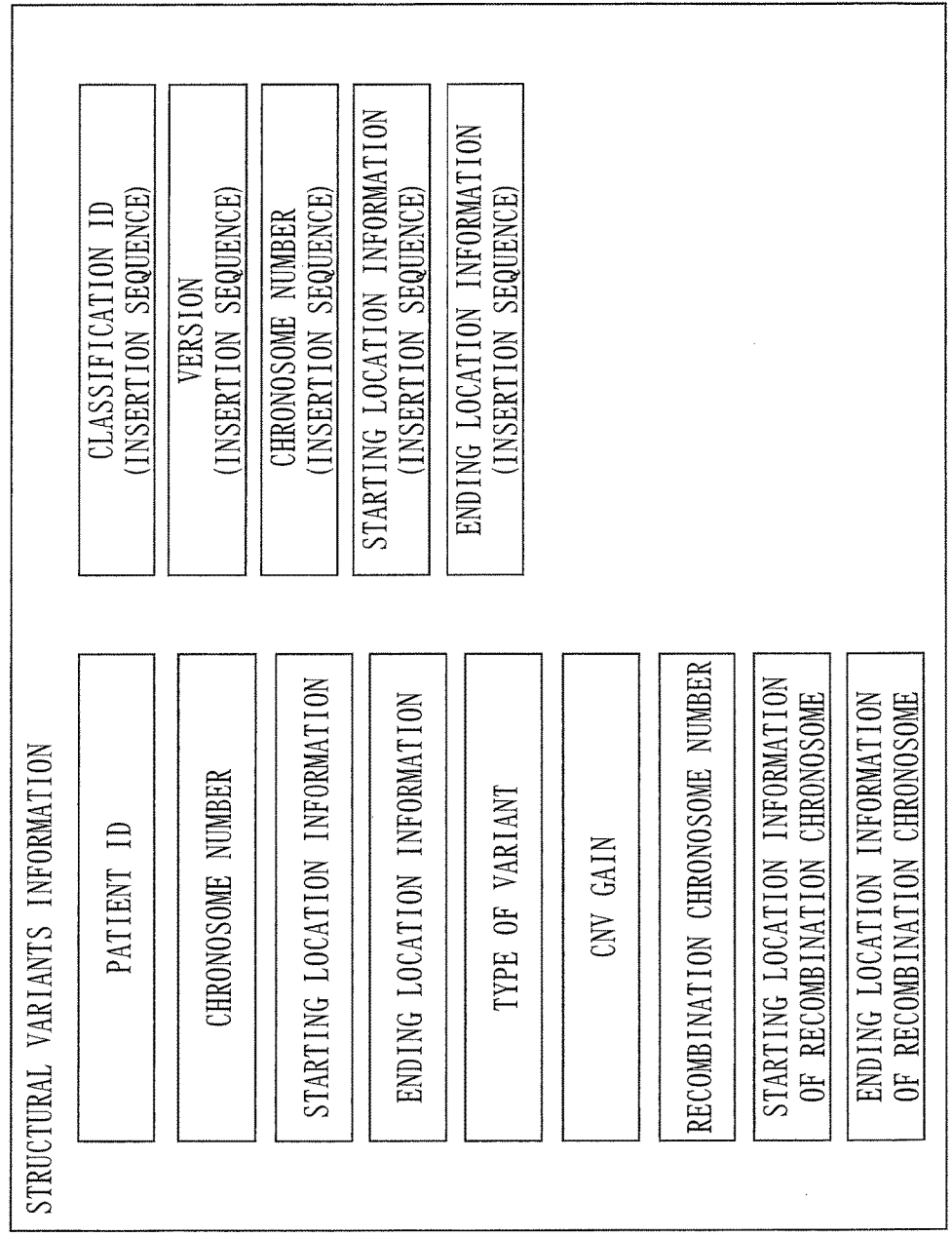
FIG. 12 is a configuration diagram of the encoded SV information.

FIG. 12 is a configuration diagram of encoded SV information.

While the SNV information indicates a case where one base is changes, the SV information indicates a case where a plurality of consecutive base sequences are changed. The SV information is composed of the patient ID, the chromosome number, starting location information, ending location information, a variant type, a CNV gain, a recombination chromosome number, starting location information of the recombination chromosome, ending location information of the recombination chromosome, a classification ID (insertion sequence), a version (insertion sequence), the chromosome number (insertion sequence), starting location information (insertion sequence), and ending location information (insertion sequence).

Since the patient ID and the chromosome number are the same as the SNV illustrated in FIG. 9, the explanation will be omitted.

The starting location information is information indicating the starting location where the change starts. In a same manner as the location information of the SNV information, the location information is divided into blocks, and a value representing the block is set.

The ending location information is information indicating the ending location where the change ends. In a same manner as the location information of the SNV information, the location information is divided into blocks, and a value representing the block is set.

The variant type is information indicating a type of the SV. For instance, "CNV gain" or "CNV loss" which represents addition/deletion of the number of repeating of the gene sequence, "Inversion" which represents an inversion of the base sequence, "Insertion" which represents large-scale insertion of the base sequence, "Deletion" which represents large-scale loss of the base sequence, "recombination" which represents recombination with another chromosome, and the like are set.

Figure 13:
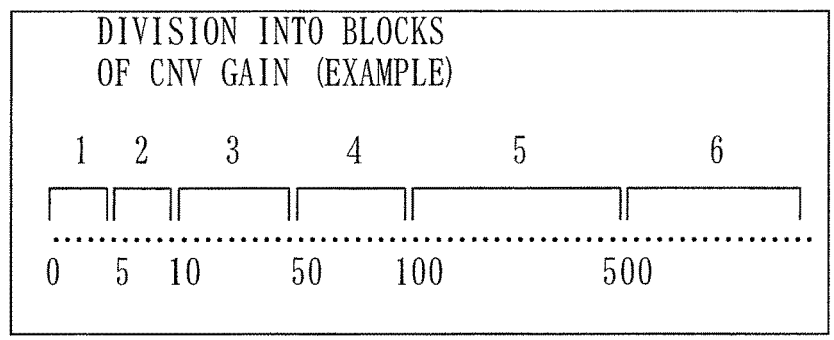
FIG. 13 is an explanatory diagram of dividing into blocks of CNV gain in the SV information.

The CNV gain is used in a case where "CNV gain" and "CNV loss" are set as the variant type. To the CNV gain, when "CNV gain" is set as the variant type, information representing how many times the number of repeating increases; and when "CNV loss" is set, information representing how many times the number of repeating decreases is set. Since this value includes integer values, the value is set by dividing into blocks. For instance, in a case where the rule is defined that division into blocks as is done as illustrated in FIG. 13, and if the CNV gain is 15, "3" which is the number of the corresponding block is set.

The recombination chromosome number is used in a case where "recombination" is specified as the variant type. To the recombination chromosome number, the number of other chromosome which has been recombined is set. The value being able to be set is the same as the chromosome number.

The starting location information of the recombination chromosome and the ending location information of the recombination chromosome are used in a case where "recombination" is specified as the variant type. The starting location information of the recombination chromosome and the ending location information of the recombination chromosome are information indicating the starting location and the ending location of the recombination with other chromosome in order to indicate with which base sequence of the other chromosome the recombination occurs. The value being able to be set is the same as the starting location information and the ending location information.

The classification ID (insertion sequence) is used in a case where "Insertion" is specified as the variant type. To the classification ID (insertion sequence), the number indicating what animate being whose base sequence is inserted is set.

The version (insertion sequence) is a numeric value indicating the version of the genome database which is used for deciding the above classification ID.

The chromosome number (insertion sequence), the starting location information (insertion sequence), the ending location information (insertion sequence) are information indicating what part of other animate being of which the base sequence has been inserted, and the values to be set is encoded in the same manner as the chromosome number, the starting location information, and the ending location information. Note that since the length of the genome sequence varies according to the animate beings type, it is preferable to prepare different ways to divide into blocks for each of the classification ID.

Further, in case of search, among the above values of the patient ID through the ending location information (insertion sequence), some values to be indicated as condition are specified, "*" (wild card) which deems any value as "matched" is indicated for the unspecified location, and thereby the differential information (search request) is generated. Base on this, the search query is generated. Then, a rule is decided, such that with respect to each element of the SV information, the search is hit when all elements are matched between the encrypted tag and the search query.

Further, it is decided under what condition each element matches.

The patient ID and the chromosome number are the same as the SNV information. The starting location information, the ending location information, the starting location information of the recombination chromosome, the ending location information of the recombination chromosome, the starting location information (insertion sequence), the ending location information (insertion sequence) can be treated as the same as the location information of the SNV information. The variant type specifies what kind of the variant type to be searched in the search query, and if the same value is set in the SV information, they are deemed as matched. The CNV gain indicates, for instance, in case of searching something in the range of 10 to 30, "3" being the number of the corresponding block is specified. Then, if the CNV gain is the same as the one included in the SV information, they are deemed as matched. The recombination chromosome number and the chromosome number (insertion sequence) can be treated as the same as the chromosome number. As for the classification ID and the version, the classification ID and the version are included in the search query, and if they are the same as the SV information, they are deemed as matched.

As discussed above, the encoding method of the SV information and a method by which the search is conducted are decided.

Figure 14:
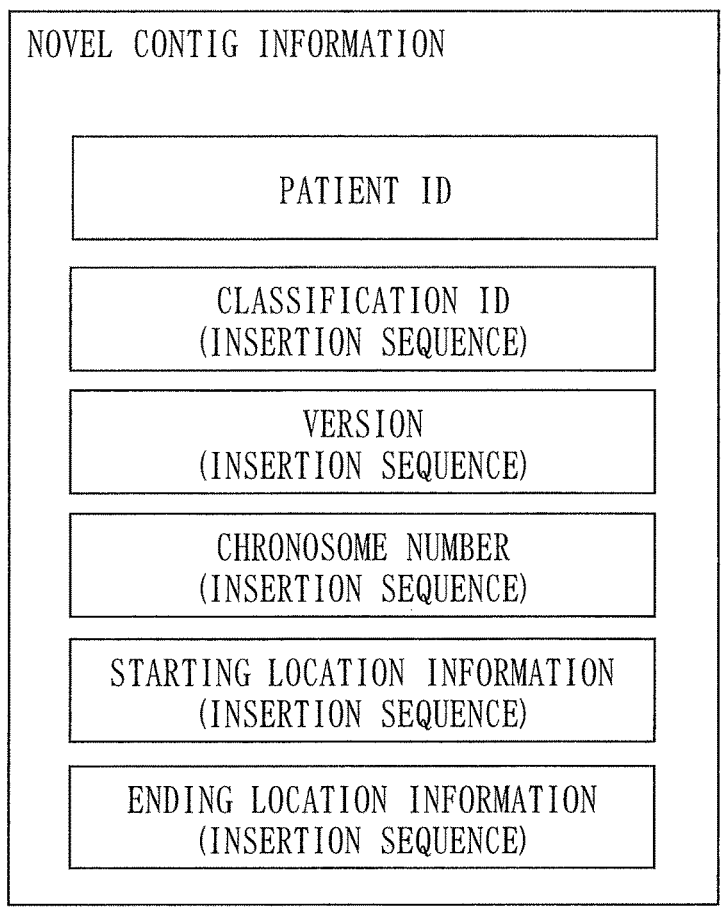
FIG. 14 is a configuration diagram of encoded NC information.

FIG. 14 is a configuration diagram of the encoded NC information.

The NC information indicates the base which is not mapped to the reference genome. When the base is not mapped to the reference genome, in many cases, it is considered a specific genome may be detected because of infection of virus and the like. Therefore, the NC information is composed of, in addition to the patient ID, the classification ID (insertion sequence), the version (insertion sequence), the chromosome number (insertion sequence), the starting location information (insertion sequence), and the ending location information (insertion sequence).

Since the method to set the values and the search method are the same as the SV information, the explanation will be omitted.

(S102: Method Decision Process)

The master key generation part 110 decides, by the processing device, the searchable encryption scheme to be used and the encryption scheme to encrypt data body. In this case, the searchable encryption scheme is required to specify a plurality of search keywords, the searchable encryption scheme using the above hierarchical predicate encryption for inner products is used. Similarly, as for the encryption scheme, the encryption scheme using the above hierarchical predicate encryption for inner products is used.

Figure 15:
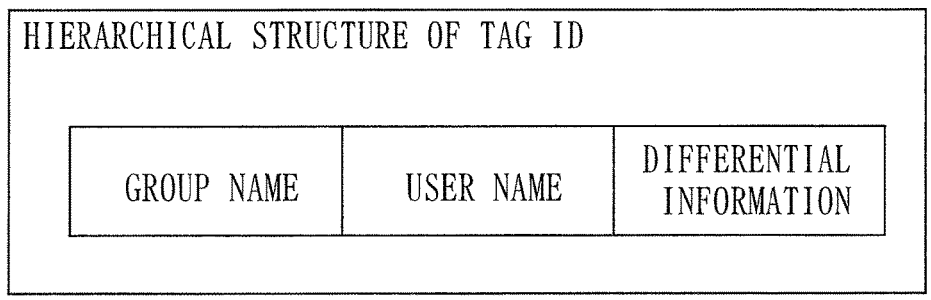
FIG. 15 is an explanatory diagram of a hierarchical structure of a tag ID.

Then, the master key generation part 110 decides a method to use the searchable encryption scheme. In this case, the hierarchical structure of the tag ID is decided. For instance, as illustrated in FIG. 15, the tag ID is composed of three elements, a group name column storing a name of a group to which the user being able to search belongs, a user name column storing a name and the like, and a differential information column storing differential information of the patient genome sequence. In case of search, a rule is defined that only when all elements of the group name, the user name, and the differential information are determined as matched, it is deemed that the search is hit.

Figure 16:
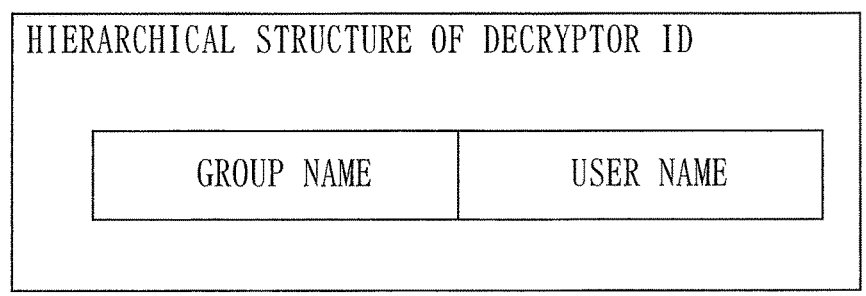
FIG. 16 is an explanatory diagram of a hierarchical structure of a decryptor ID.

Similarly, the master key generation part 110 decides a method to use the encryption scheme for encrypting the data body. In this case, the hierarchical structure of the decryptor ID is decided. For instance, as illustrated in FIG. 16, the decryptor ID is composed of two elements, that is, a group name column storing a name of a group to which the user being able to decrypt belongs and a user name column storing a name and the like. In case of decryption, a rule is defined that only when all of the group name and the user name are matched, the user can decrypt.

(S103: User ID Storage Process)

The user ID storage part 150 builds a user ID information database storing the user ID. The user ID information database is to store information being necessary to generate the user private key and information being necessary to specify the group name/the user name of a partner when the encryption apparatus 200 encrypts data.

For instance, as illustrated in FIG. 17, the user ID information database store a company name which is the group name, a name which is the user name, the affiliation information, the valid term, and the like. Further, the user ID information database may store not only the latest status but all of the history.

(S104: Master Key Generation Process)

The master key generation part 110 executes, by the processing device, the master key generation algorithm of the searchable encryption scheme, to generate the master key for the searchable encryption and the public parameter for the searchable encryption. Similarly, the master key generation part 110 executes, by the processing device, the master key generation algorithm of the encryption scheme, to generate the master key for encryption and the public parameter for encryption.

Hereinafter, the master key for the searchable encryption and the master key for encryption are united and called as the master key, and the public parameter for the searchable encryption and the public parameter for encryption are united and called as the public parameter.

(S105: Master Key Storage Process)

The key storage part 120 stores the master key and the public parameter generated by the master key generation part 110 in the storage apparatus.

(S106: Public Parameter Opening Process)

The data transmission/reception part 140 opens the public parameter stored by the key storage part 120 to the encryption apparatus 200, the search apparatus 300, and the data center 400 via the network 500.

Here, the opened public parameter is stored by the public parameter storage part 230 in the encryption apparatus 200, by the user private key storage part 320 in the search apparatus 300, and by the public parameter storage part 450 in the data center 400.

By the above procedure, the setup of the gene search system 10 has been completed.

Here, as for the user ID information database generated at S103, the contents are maintained every personnel movement, entry, or retirement of the user in the operation of the system.

Figure 18:
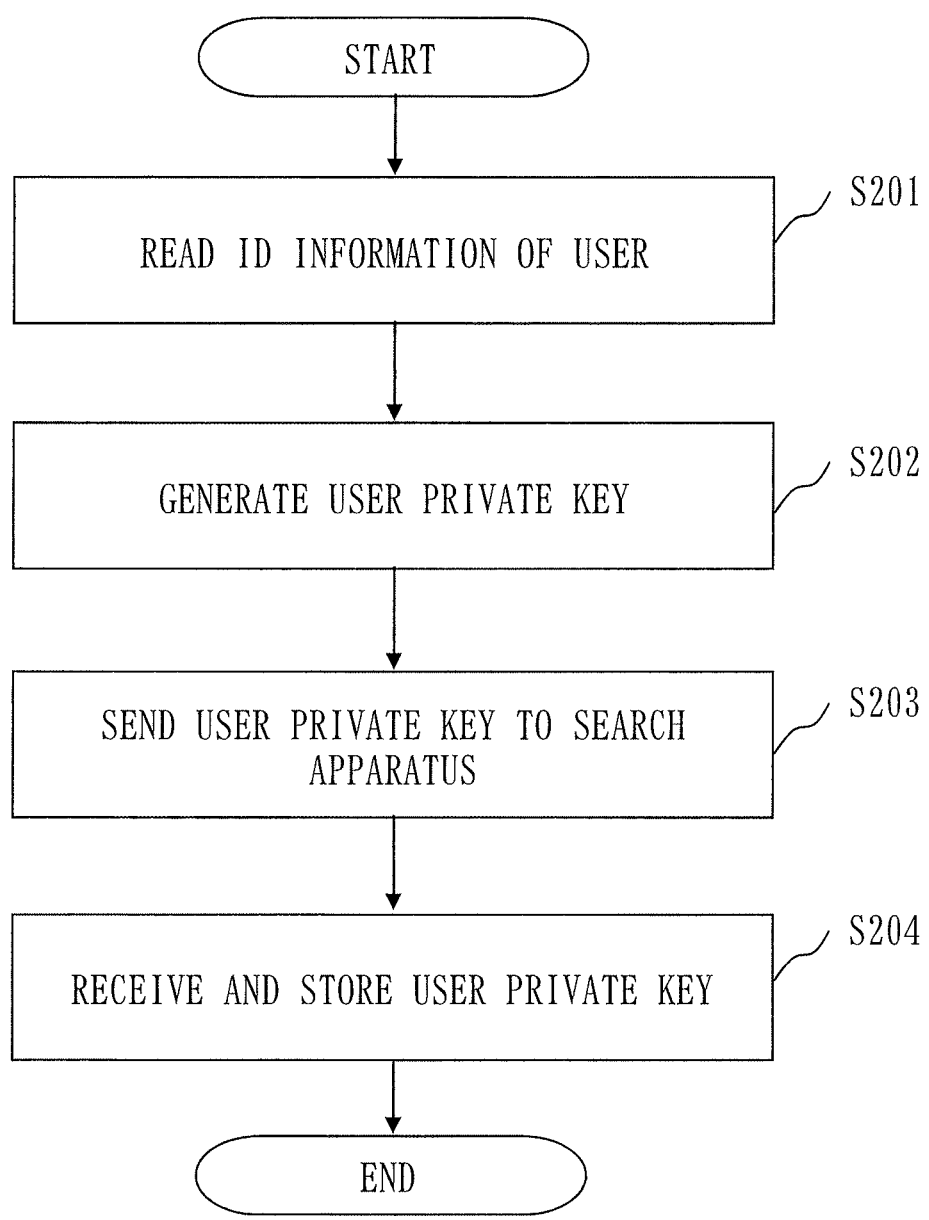
FIG. 18 is a flowchart illustrating a flow of a user private key issuance process.

FIG. 18 is a flowchart illustrating a flow of the user private key issuance process.

The user private key issuance process is a process to be carried out mainly by the key management server 100 and the search apparatus 300 when a new user is added or when the name of the group to which the user belongs is changed.

(S201: User ID Obtainment Process)

The user private key generation part 130 obtains, from the user ID information database held by the user ID storage part 150, the group name and the user name of the user to whom a user private key is issued.

(S202: User Private Key Generation Process)

The user private key generation part 130 generates, by the processing device, the user private key for the searchable encryption which is used for generating the search query and the user private key for encryption which is used for decrypting the encrypted data.

According to the searchable encryption scheme, when the user private key for the searchable encryption is generated, the tag ID hierarchical structure should be specified. In this case, the group name obtained at S201 is set to the group name, similarly, the user name is set to the user name, the differential information is specified as a delegatable element so that the user who conducts search afterwards can set, and thereby the user private key for the searchable encryption is generated.

Similarly, when generating the user private key for encryption using the encryption scheme, it is necessary to specify the decryptor ID hierarchical structure. In this case, the group name obtained at S201 is set to the group name column, and similarly, the user name is set to the user name, and thereby the user private key for encryption is generated.

The user private key for the searchable encryption and the user private key for encryption which have been generated above are united and called as the user private key.

(S203: User Private Key Transmission Process)

The data transmission/reception part 140 sends the user private key generated at S202 to the search apparatus 300.

(S204: User Private Key Reception Process)

The user private key storage part 320 receives the user private key sent at S203 and stores the user private key in the storage apparatus.

Figure 19:
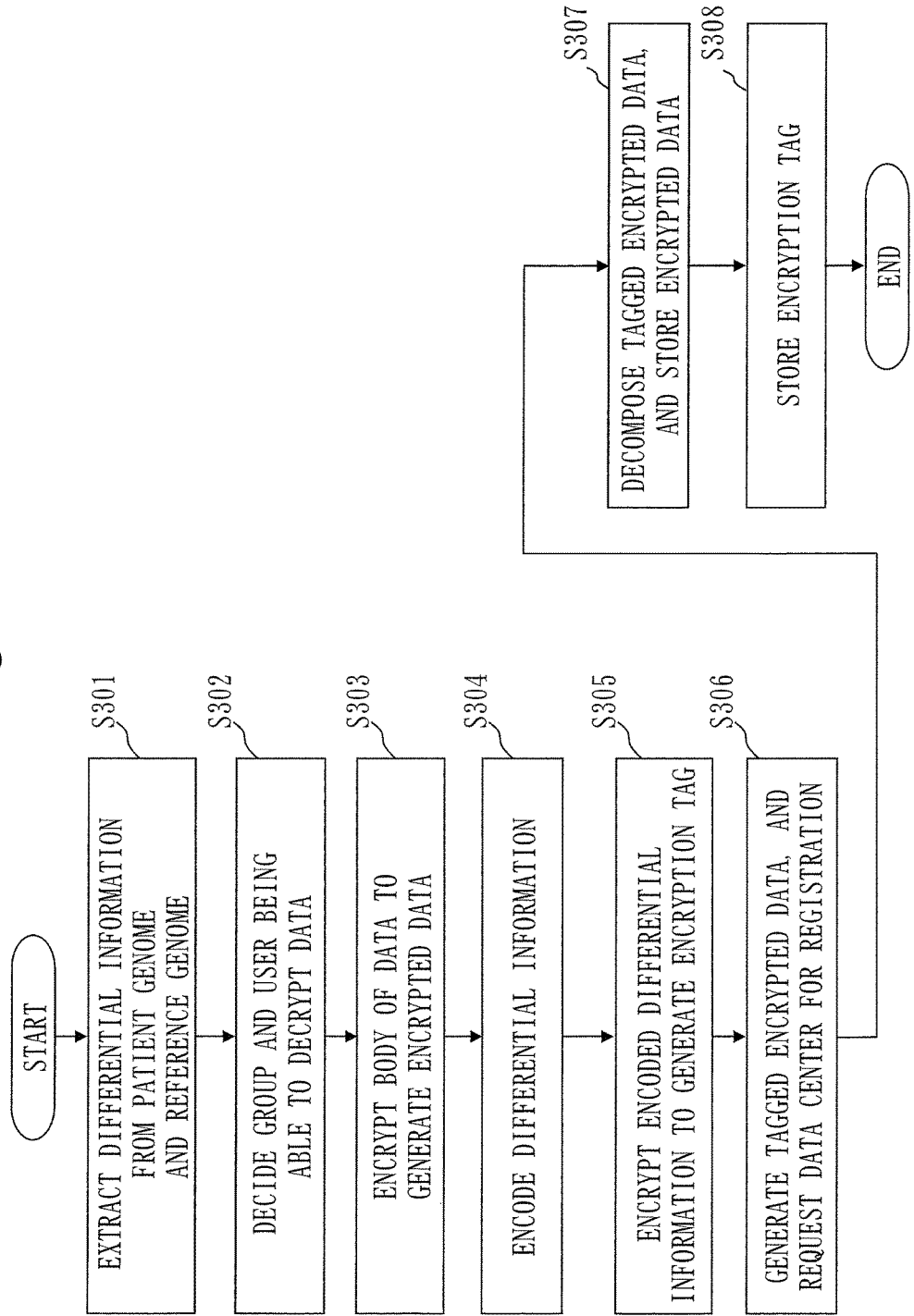
FIG. 19 is a flowchart illustrating a flow of an encryption process of a patient genome sequence.

FIG. 19 is a flowchart illustrating a flow of the encryption process of the patient genome sequence.

The encryption process of the patient genome sequence is mainly executed by the encryption apparatus 200 and the data center 400 when the patient genome sequence is encrypting and stored in the data center 400.

(S301: Differential Information Extraction Process)

The reference gene obtainment part 210 obtains, for instance, the reference genome sequence which is opened on the Internet. Further, the target gene input part 220 receives, by the inputting device, the patient genome sequence.

The differential information generation part 240 compares, by the processing device, the patient genome sequence with the reference genome sequence, to generate the differential information such as SNV, SV, NC, and the like. As for a method to generate the differential information, ChIP-seq method, RNA-seq method, MeDIP-seq method, the mutation analysis method, or the bisulfate method, and the like are known; such a general method is used.

(S302: User Determination Process)

The data encryption part 260 makes the user who operates the encryption apparatus 200 enter the group name and the user name of the user being able to decrypt the encrypted data. Similarly, the encrypted tag generation part 270 makes the user enter the group name and the user name of the user being able to search the encrypted data.

The group name and the user name is not necessarily one, a plurality of the group names and the user names can be entered when there exist a plurality of users being able to decrypt or search. Here, according to the searchable encryption scheme and the encryption scheme which are used here, the wild card which means any one can be obtained for the group name and the user name.

(S303: Data Encryption Process)

The data encryption part 260 encrypts, by the processing device, using the group name and the user name who is able to decrypt received at S302, the patient genome sequence received at S301.

Specifically, the data encryption part 260 generates the session key at random, encrypts the patient genome sequence using a common key encryption such as AES, Camellia (registered trademark) by the session key, to generate the encrypted data body. Next, the data encryption part 260 specifies the group name and the user name of the user being able to decrypt entered at S302 to the group name and the user name of the decryptor ID hierarchical structure, respectively, and using this as the public key for encryption, and encrypts the session key using the encryption scheme decided at S102, to generate the encryption session key. Then, the data encryption part 260 combines the above two encrypted results (the encrypted data body and the encryption session key), to generate the encrypted data.

Figure 20:
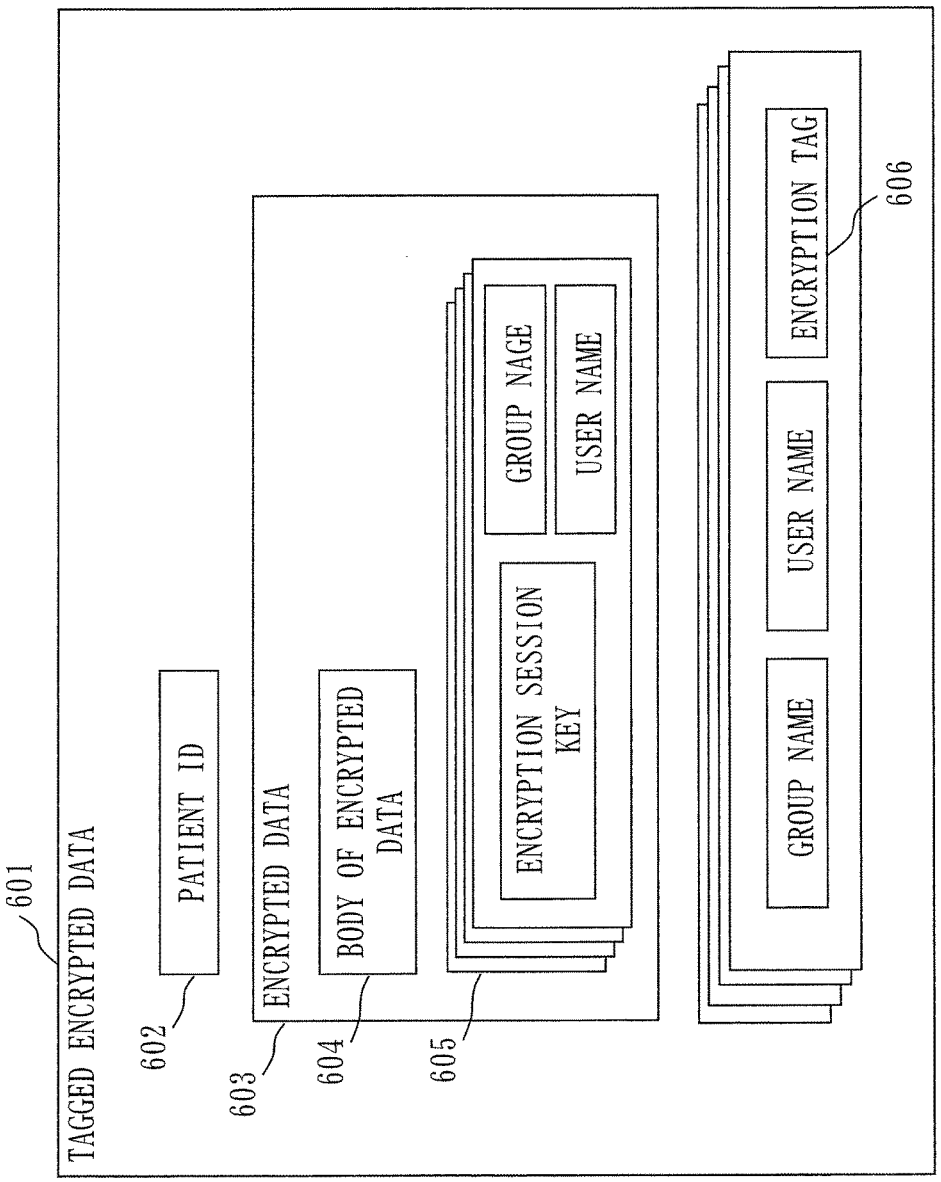
FIG. 20 is an explanatory diagram of tagged encrypted data.

Data configuration of the generated encrypted data is illustrated in FIG. 20 at the sign of 603. Here, if, at S302, the plurality of group names and user names are received, the encryption session key has to be generated with respect to each combination of the group name and the user name.

(S304: Differential Information Encoding Process)

The differential information encoding part 250 encodes, by the processing device, each differential information generated at S301 according to the encoding method decided at S101, to generate the encoded differential information. Further, the differential information encoding part 250 makes the user enter the patient ID, and the patient ID is included in the encoded differential information.

(S305: Encrypted Tag Generation Process)

The encrypted tag generation part 270 encrypts the encoded differential information, to generate the encrypted tag.

Specifically, the encrypted tag generation part 270 specifies, by the processing device, the group name and the user name of the user being able to search entered at S302 to the group name and the user name of the tag ID hierarchical structure, specifies the encoded differential information encoded at S304 to the differential information column, encrypts the random number value using the searchable encryption scheme, to generate the encrypted tag. Further, the encrypted tag generation part 270 includes the random number value in the encrypted tag, while the random number value being plaintext.

Note that since the above process is for one piece of the differential information, the process is implemented with respect to each piece of the encoded differential information. For instance, the process is implemented with respect to each of the encoded differential information such as SNV, SV, and NC. Further, if at S302, a plurality of combinations of the group name the user name is received, the encrypted tag is generated with respect to each combination of the group name and the user name.

(S306: Storage Request Process)

The tagged encrypted data generation part 280 combines, by the processing device, the encrypted data generated at S303, the encrypted tag generated at S305, and the patient ID entered at S304, to generate the tagged encrypted data (the sign 601 of FIG. 20). Then, the tagged encrypted data generation part 280 sends the generated tagged encrypted data to the data center 400 to request for storage.

At this time, in order to facilitate to store the tagged encrypted data in the data center 400, the tagged encrypted data generation part 280 sends the group name and the user name of the user being able to decrypt entered at S302 and the group name and the user name of the user being able to search together. In the configuration of the tagged encrypted data illustrated in FIG. 20, the group name and the user name of the user being able to decrypt and the group name and the user name of the user being able to search are included in the tagged encrypted data.

(S307: Encrypted Data Storage Process)

The storage request processing part 410 decomposes, by the processing device, the tagged encrypted data received from the encryption apparatus 200, and extracts the encrypted data, a plurality of encrypted tags, and the patient IDs. Then, the storage request processing part 410 makes the encrypted data storage part 420 store the encrypted data with the patient ID.

Here, the encrypted data storage part 420 stores the encrypted data for each of the group name and the user name included in the tagged encrypted data, further appends the management number to the stored encrypted data so that the encrypted data should be uniquely identified from the management number later. In a case where the encrypted data is made related to the plurality of group names and user names, the encrypted data is stored with related to each group name and user name. When related to the plurality of group names and user names, only one piece of encrypted data is stored, and only reference information is stored for the other, and thereby the capacity of the disk can be reduced.

FIG. 21 illustrates a storage example of the encrypted data. As illustrated in FIG. 21, the storage request processing part 410 manages the encrypted data whose group name is "pharmaceutical company A" and whose user name is "*" (wild card), the patient ID, and the management number unitedly; and the encrypted data whose group name is "hospital B" and whose user name is "*", the patient ID, and the management number unitedly. Further, in a case where some data is disclosed to both of pharmaceutical company A and hospital B, for instance, the patient ID and the encrypted data body is stored with related to the management number 000001; and in addition to the patient ID, a pointer indicating to reference to the management number 000001 for the encrypted data is stored in the management number 100002.

(S308: Encrypted Tag Storage Process)

The storage request processing part 410 makes the encrypted tag storage part 430 store the plurality of encrypted tags extracted at S307 together with the management number and the patient ID of the corresponding encrypted data. The encrypted tag storage part 430 stores the encrypted tag, the management number, and the patient ID by separating them with each of the group name and the user name included in the tagged encrypted data.

Figure 22:
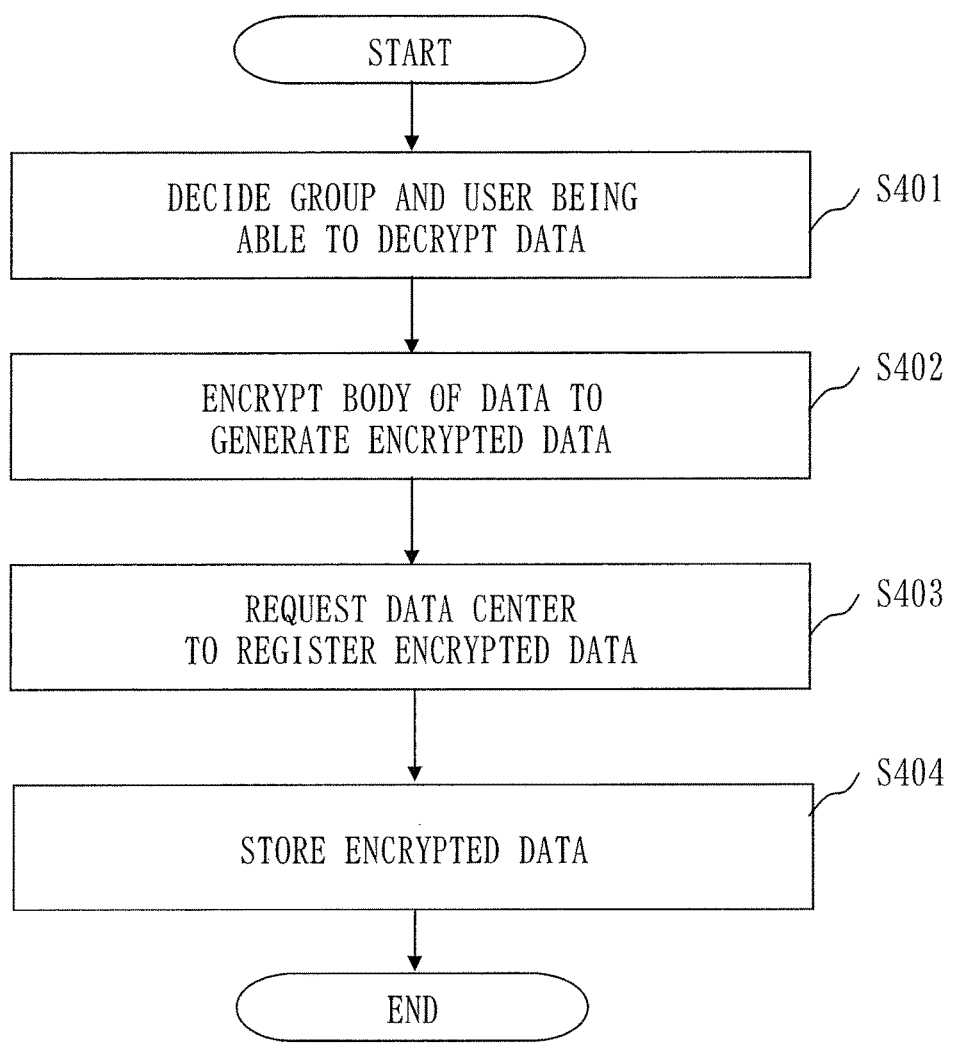
FIG. 22 is a flowchart illustrating a flow of an encryption process of an electronic health record of a patient.

FIG. 22 is a flowchart illustrating a flow of the encryption process of the electronic health record of the patient.

The encryption process of the electronic health record of the patient is a process which is implemented mainly by the encryption apparatus 200 and the data center 400, and the process is implemented at the time of encrypting the electronic health record and storing the electronic health record in the data center 400.

(S401: User Decision Process)

The data encryption part 260 makes the user who operates the encryption apparatus 200 enter the group name and the user name of the user being able to decrypt the electronic health record.

The group name and the user name entered here is not necessarily limited to one, but a plurality of the group names and the user names can be entered if there are a plurality of the users being able to decrypt.

(S402: Data Encryption Process)

The data encryption part 260 makes the user enter the patient ID and the electronic health record. Then, the data encryption part 260 encrypts, by the processing device, the electronic health record using the group name and the user name received at S401. Since the specific encryption method is the same as a flow of encrypting the patient genome sequence at S303, the detail will be omitted.

(S403: Storage Request Process)

The data encryption part 260 sends the encrypted data generated at S402, together with the patient ID representing the owner of the electronic health record and the group name and the user name of the user being able to decrypt, to the data center 400 to request for storage.

(S404: Encrypted Data Storage Process)

The storage request processing part 410 makes the encrypted data storage part 420 store the encrypted data received from the encryption apparatus 200 with related to the patient ID.

Figure 23:
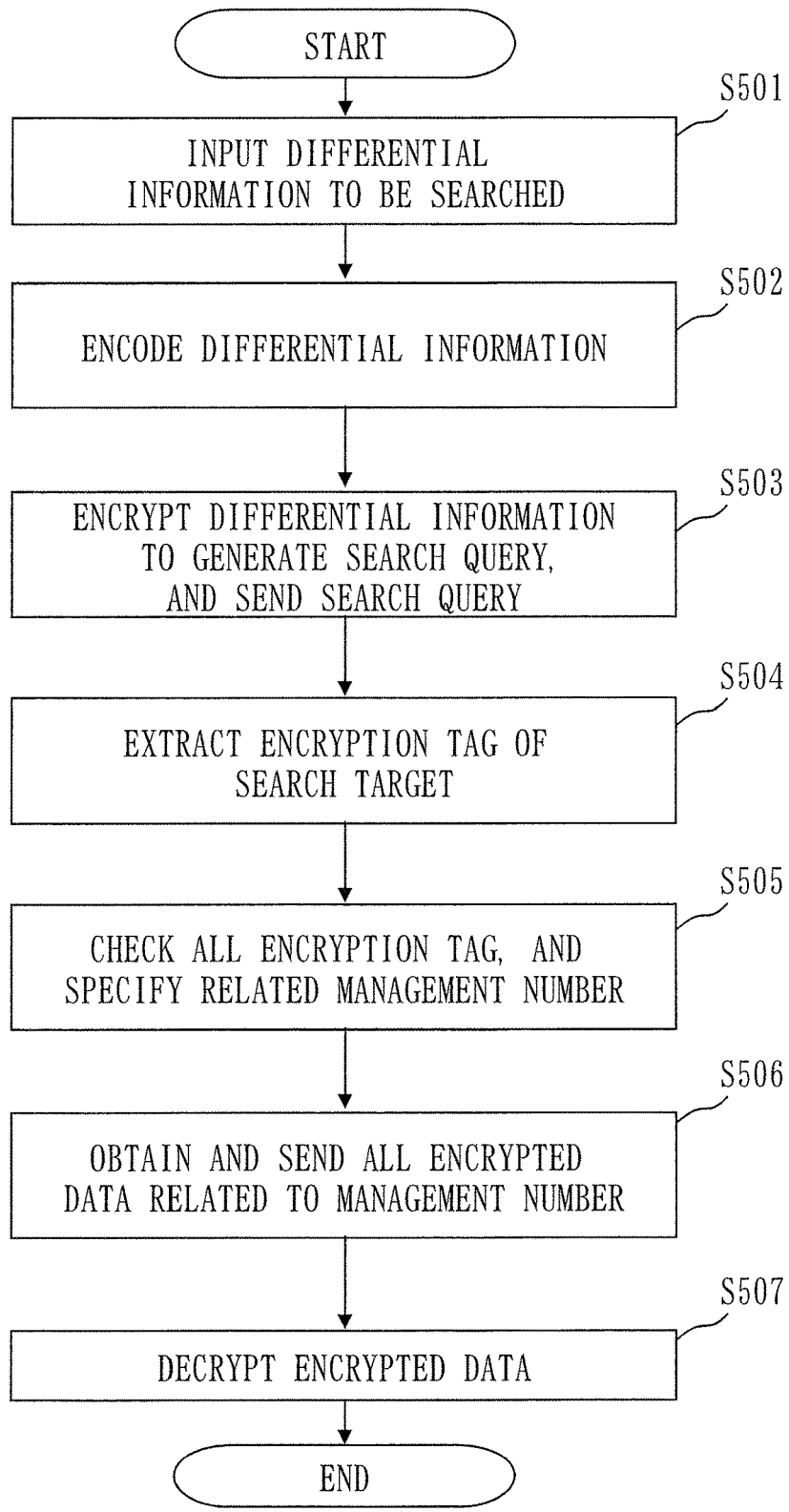
FIG. 23 is a flowchart illustrating a flow of a search process.

FIG. 23 is a flowchart illustrating a flow of the search process.

The search process is a process executed by mainly the search apparatus 300 and the data center 400 when the encrypted patient genome sequence stored in the data center 400 is obtained.

(S501: Differential Information Inputting Process)

The differential information input part 310 makes the user who operates the search apparatus 300 enter a search request including the differential information with the reference genome sequence as the search keyword.

The differential information entered here does not necessarily specify all elements like the differential information extracted from the patient genome, for instance, only the chromosome number can be specified, or only the location information can be specified.

(S502: Differential Information Encoding Process)

The differential information encoding part 330 encodes, by the processing device, the differential information entered at S501, to generate the encoded differential information. Since this process is the same as the process of step S304, the detail will be omitted. However, it is noted that "*" should be set to the unspecified element.

(S503: Search Query Generation Process)

The search query generation part 340 generates, by the processing device, the search query using the encoded differential information generated at S502 and the user private key stored in the user private key storage part 320. Then, the search query generation part 340 sends the generated search query to the data center 400.

At this time, the search query generation part 340 also sends the group name and the user name of the user himself. Here, in order to verify the reliability the group name and the user name, a user authentication of the user who operates the search terminal is also conducted.

(S504: Encrypted Tag Extraction Process)

The search request processing part 440 obtains, by the processing device, all the encrypted tags which are searchable using the group name and the user name sent at S503 together with the search query from all the encrypted tags stored in the encrypted tag storage part 430. Further, the search request processing part 440 extracts a list of the patient IDs which are accessible by the group name and the user name of the corresponding the patient ID from the access authority storage part 460, and narrows down the obtained encrypted tag to only the encrypted tag.

Here, the access authority storage part 460 includes an access authority management table as illustrated in FIG. 24, using the group name and the user name as the accessor information, specifies the patient ID related to the searchable patient genome sequence, and outputs the encrypted tag related to the patient ID.

(S505: Match Checking Process)

The search request processing part 440 carries out, by the processing device, the match checking process of the searchable encryption scheme on the encrypted tag narrowed at S504 to check whether or not the differential information included in the encrypted tag matches the condition specified by the differential information included in the search query sent at S503.

The match checking process of the searchable encryption scheme only implements comparison of one encrypted tag with one search query. Therefore, the match checking process is implemented on all the encrypted tags obtained at S504. Then, as a result of checking process, the management number related to the encrypted tag which has been determined as matched is specified.

(S506: Encrypted Data Obtainment Process)

The search request processing part 440 obtains all the encrypted data corresponding to the management number specified at S505 from the encrypted data storage part 420, and sends the encrypted data together with the related patient ID to the search apparatus 300.

(S507: Encrypted Data Decryption Process)

The data decryption part 360 carries out, by the processing device, the decryption process of the encryption scheme using the user private key for encryption stored by the user private key storage part 320, thereby decrypting the encrypted data received at S506 from the data center 400. The data decryption part 360 implements this process on all the received encrypted data.

With the above procedure, the search apparatus 300 receives the differential information to be searched from the user, obtains the encrypted data which matches the differential information from the data center 400, and decrypts the encrypted data, thereby browsing the patient genome sequence. Further, according to the necessity, the patient ID corresponding to the encrypted data is sent to the data center 400, and the corresponding electronic health record and the like can be obtained.

As discussed above, according to the gene search system 10 of the first embodiment, the patient genome is encrypted using the searchable encryption scheme, and stored in the data center 400; and further the search request is also encrypted using the searchable encryption technique, and requests the data center 400 to search. Therefore, knowing nothing about the contents of the patient genome, the data center 400 can provide the search service.

Further, the human genome information is extremely large data composed of three billions of bases. Therefore, if all the human genome information are made as tags, in addition to the fact that the data size is further increased due to the encryption, such an operation may cause compress the disk capacity or the network capacity. However, according to the gene search system 10 of the first embodiment, only the differential information with the reference genome sequence which is laid open in public is made as tags, which reduces largely the disk capacity or the network capacity.

Further, according to the gene search system 10 of the first embodiment, the numeric value information such as the location information and the reliability of the SNV are divided into blocks, which enables the range search that has been difficult to carried out in the searchable encryption using the match search. Therefore, the gene search system 10 of the first embodiment can be adapted to the range search which is used by the genome search.

In particular, in the location information of the SNV illustrated in FIG. 10, each block is made overlapped. That is, the block 1 and the block 2 are overlapped from the location 5000 to 10000; the block 2 and the block 3 are overlapped from the location 10000 to 15000. By these overlaps, if the range specified at the time of search is equal to or less than 5000, the search is conducted using all the blocks; if the range specified at the time of search is equal to or less than 10000, the search is conducted using only the odd-numbered blocks, which enables a high-speed processing.

Further, according to the gene search system 10 of the first embodiment, even if a plurality of search conditions such as the chromosome number or the location information are specified, the matching check of the condition is not carried out individually, but whether or not all the search conditions are satisfied is checked as a whole using the predicate encryption for inner products. Therefore, the server does not recognize that the search is partially hit, which means high security.

Further, according to the gene search system 10 of the first embodiment, the patient ID is included together with the encrypted data. Therefore, the information such as the related electronic health record can be extracted from the patient ID which is obtained as a search result. Therefore, in a case where mutation occurs in the corresponding base, it is possible to research what kind of diseases to which the mutation relates to.

Further, according to the gene search system 10 of the first embodiment, in case of encrypting the differential information of the patient genome sequence, the group name and the user name are included with respect to the tag ID hierarchical structure and the decryptor ID hierarchical structure. Therefore, it is possible to limit a researcher or a doctor who is allowed to search or decrypt. For instance, if "pharmaceutical company A" is specified to the group name, and the wild card "*" is specified to the user name, the information of such a patient can be limited to the company employees of pharmaceutical company A. Further, when the encryption is performed by specifying the wild card "*" to both of the group name and the user name, the information of the patient can be used by the doctors or the researchers registered in the system.

Further, according to the gene search system 10 of the first embodiment, separately from the access control by the cipher, the access authority management table is held by the data center 400, which enables to carry out the access control based on the information of the access authority management table. Therefore, according to the request from the patient, browsing of the information can be managed in detail such as "able to browse only the genome sequence" or "able to browse the health record" and the like. That is, whether or not the search request for the patient genome sequence is allowed is determined based on this information, and thereby precise access control is enabled.

Further, according to the gene search system 10 of the first embodiment, the group name and the user name are included with respect to the user private key of the searcher. Therefore, the group name and the user name included in the search query generated from the user private key is checked, and thereby the authentication is carried out.

Note that the above explanation describes a case where the access control is carried out in units of a company. However, this unit of access control is merely an example. For instance, a condition of national qualification such as a doctor or a nurse may be included, or a flag representing whether or not the searcher is a participant to the national project may be set. These ID hierarchical structures are merely examples, and various elements can be added or some elements can be deleted.

Further, the above explanation assumes a case where a nation manages only one key management server 100, and the sequencer operator who analyzes the genome on behalf of the doctor uses the encryption apparatus 200. However, according to the system to be used, it is possible to flexibly change the system configuration. For instance, the doctor who receives the detection result from the sequencer operator may operate the encryption apparatus 200, and may encrypt the patient genome sequence.

Further, in the above explanation, the user private key is stored in the search apparatus 300, which enables the search apparatus 300 to generate the search query or to decrypt the encrypted data. However, in order to increase the security, the management of the user private key is carried out by not the search apparatus 300, but by devices such as an IC card. In this case, the user private key is securely managed within the IC card, thereby increasing the security.

Further, in the above explanation, the user private key for the searchable encryption to be used by the search terminal is generated as a key which can be commonly used in the search of the SNV information, the SV information, the NC information, and the like. However, since the length of each differential information vary, in place of using the common user private key for the searchable encryption, the user private key for the searchable encryption, such as the SNV information the user private key for the searchable encryption, the SV information the user private key for the searchable encryption, the NC information the user private key for the searchable encryption, and the like, may be individually generated according to the usage. In this case, the length of the user private key for the searchable encryption is optimized according to the length of each information, thereby increasing the speed of the calculation time.

Further, in the above explanation, the character strings such as "pharmaceutical company A" or "TANAKA" are used to indicate the group name or the user name. This is to facilitate the understanding of the embodiment in a preferential manner, and actually not only character strings, but ID such as numbers can be used. The same can be applied to other elements such as the chromosome number.

Further, the above explanation describes a case where the hierarchical predicate encryption for inner products is used for the searchable encryption scheme or the encryption scheme. However, the encryption is not limited to the hierarchical predicate encryption for inner products as long as it includes the same function. Further, different methods can be used for the searchable encryption scheme and for the encryption scheme.

Further, in the above explanation, the user ID storage part 150 is able to also manage the attribute information of the user in the past. Such a management should be implemented only when administratively necessary, and it may be sufficient to manage only the attribute information at present.

Further, the above explanation describes the embodiment which is implemented assuming that all the users use one common reference genome sequence. However, it is also possible to implement the embodiment by using different reference genomes. In this case, for the encryption, the differential information can be generated with respect to all the reference genome sequences, for the search, the differential information with any one of the reference genome sequences can be set as the search query; it is also possible to generate the differential information with one reference genome sequence for encryption, and to set the differential information with all the reference genome sequences to the search query.

Further, in the above explanation, for the information which requires the range search such as the location information, the reliability, the CNV gain, and the like, the checking process can be done by complete match of the keyword by dividing such information into blocks. However, since the range to be searched may vary according to the usage, it is not always required that the search can be done by the complete match. For instance, while the search range is specified to belong to the block 10 at the time of encryption, it is also possible to specify a plurality of blocks such as the block 10 or the block 11 at the time of search.

Further, in the above explanation, it is assumed that there is only one key management server 100. However, the hierarchical predicate encryption for inner products which is used for the searchable encryption scheme or the encryption scheme can be applied to a case where the key management server 100 is stratified and distributed into a plurality. Therefore, also in such a case, it is possible to stratify the key management server 100 to be operated.

Further, the above explanation describes an example in which, as the differential information, the SNV information, the SV information, and the NC information are encrypted. However, with a similar structure, differential information other than the above can be encrypted.

Figure 25:
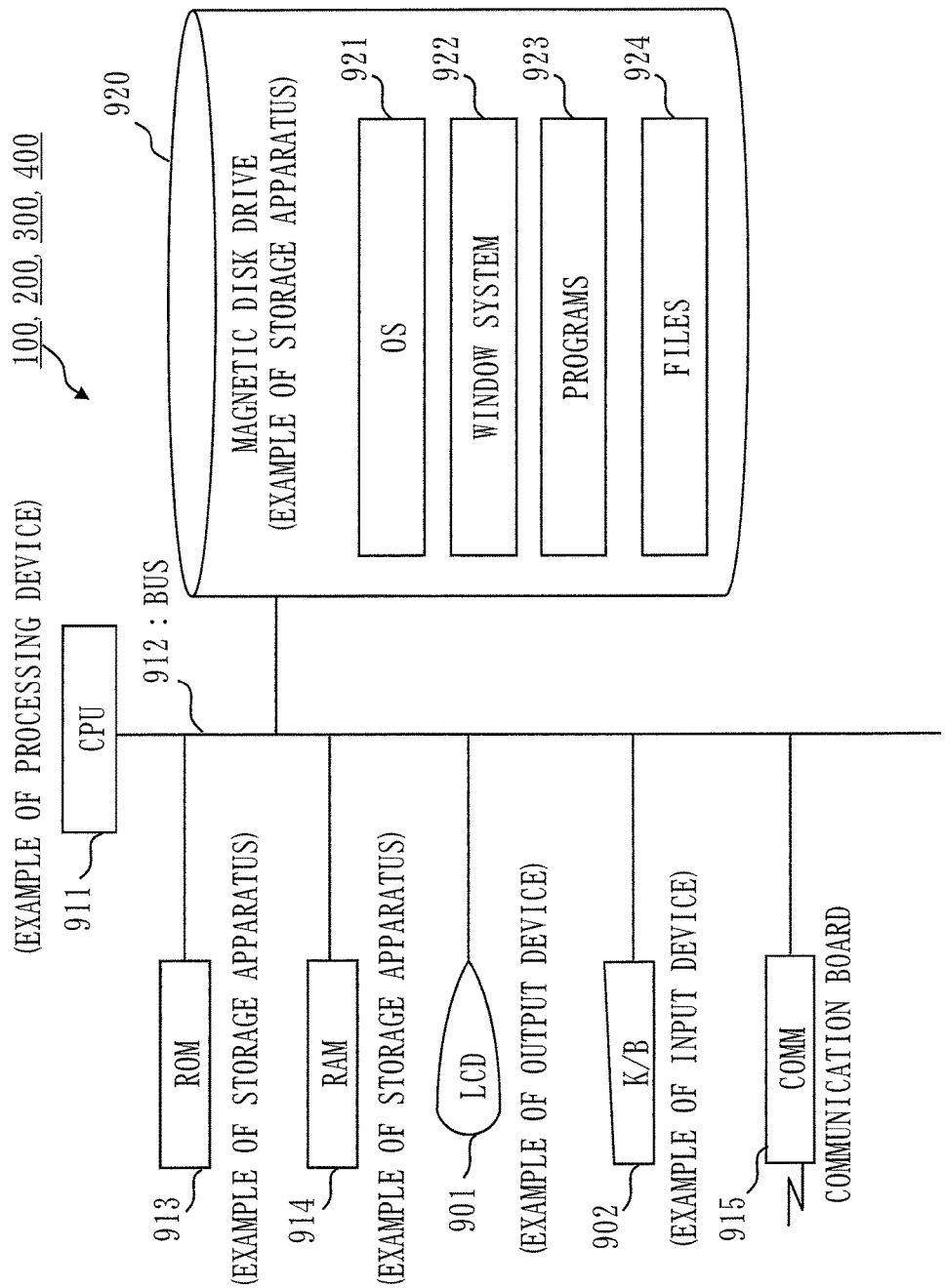
FIG. 25 illustrates an example of hardware configuration of the key management server 100, the encryption apparatus 200, the search apparatus 300, and the data center 400.

FIG. 25 is a diagram illustrating an example of hardware configuration of the key management server 100, the encryption apparatus 200, the search apparatus 300, and the data center 400.

As illustrated in FIG. 25, the key management server 100, the encryption apparatus 200, the search apparatus 300, and the data center 400 are provided with a CPU 911 (also called as a Central Processing Unit, a central processing device, a processing device, a calculation device, a microprocessor, a microcomputer, or a processor) which executes programs. The CPU 911 is connected to a ROM 913, a RAM 914, a LCD 901 (Liquid Crystal Display), a keyboard 902 (K/B), a communication board 915, and a magnetic disk drive 920 via a bus 912, and controls these hardware devices. In place of the magnetic disk device 920 (a fixed disk drive), a storage device such as an optical disk device or memory card read/write device may be employed. The magnetic disk device 920 is connected via a predetermined fixed disk interface.

The ROM 913 and the magnetic disk drive 920 are examples of a non-volatile memory. The RAM 914 is an example of a volatile memory. The ROM 913, the RAM 914, and the magnetic disk drive 920 are examples of a storage apparatus (memory). Further, the keyboard 902 and the communication board 915 are examples of an input device. Further, the communication board 915 is an example of a communication device. In addition, the LCD 901 is an example of a display device.

The magnetic disk drive 920, the ROM 913, and the like store an operating system 921 (OS), a window system 922, programs 923, and files 924. Programs of the programs 923 are executed by the CPU 911, the operating system 921, and the window system 922.

The programs 923 store software or programs that execute the functions described as the "master key generation part 110", the "user private key generation part 130", the "data transmission/reception part 140", the "reference gene obtainment part 210", the "target gene input part 220", the "differential information generation part 240", the "differential information encoding part 250", the "data encryption part 260", the "encrypted tag generation part 270", the "tagged encrypted data generation part 280", the "differential information input part 310", the "differential information encoding part 330", the "search query generation part 340", the "genetic information obtainment part 350", the "data decryption part 360", the "storage request processing part 410", the "search request processing part 440", and the like in the above explanation and other programs. The programs are read and executed by the CPU 911. The files 924 store information, data, signal values, variable values, or parameters to be stored in the "key storage part 120", the "user ID storage part 150", the "public parameter storage part 230", the "user private key storage part 320", the "encrypted data storage part 420", the "encrypted tag storage part 430", the "public parameter storage part 450", the "access authority storage part 460", and the like in the above explanation as a "file" or each entry of a "database". The "file" or the "database" is stored in storage medium such as a disk or a memory. The information, data, signal values, variable values, or parameters stored in the disk or the memory is read out to a main memory or a cache memory via a reading/writing circuit by the CPU 911, and used for the operation of the CPU 911 such as extraction, search, reference, comparison, calculation, computation, processing, output, printing, display, and the like. During the operation of the CPU 911 such as extraction, search, reference, comparison, calculation, computation, processing, output, printing, and display, the information, data, signal values, variable values, or parameters are temporarily stored in the main memory, the cache memory, and the buffer memory.

Further, the arrows in the flowcharts in the above explanation mainly represent input/output of data and signals. The data and signal values are stored in the memory of the RAM 914, the recording medium such as an optical disk, or in an IC chip. The data and signals are transmitted online via a transmission medium such as the bus 912, signal lines, or cables; or electric waves.

Further, a "part" in the above explanation may be a "circuit", "device", "equipment", "means" or "function"; or a "step", "procedure", or "process". A "device" or a "terminal" may be a "circuit", "equipment", "means", or "function"; or a "step", "procedure", or "process". Further, a "process" in the explanation may be a "step". Namely, a "part" may be realized as firmware stored in the ROM 913. Alternatively, a "part" may be implemented by only software; by only hardware such as an element, a device, a substrate, or a wiring line; by a combination of software and hardware; or furthermore by a combination of software, hardware, and firmware. The firmware and software are stored, as programs, in the recording medium such as the ROM 913. The program is read by the CPU 911 and executed by the CPU 911. Namely, the program causes the computer or the like to function as a "part" described above. Alternatively, the program causes the computer or the like to execute the procedure and method of the "part" described above.

REFERENCE SIGNS LIST

10: gene search system; 100: key management server; 110: master key generation part; 120: key storage part; 130: user private key generation part; 140: data transmission/reception part; 150: user ID storage part; 200: encryption apparatus; 210: reference gene obtainment part; 220: target gene input part; 230: public parameter storage part; 240: differential information generation part; 250: differential information encoding part; 260: data encryption part; 270: encrypted tag generation part; 280: tagged encrypted data generation part; 300: search apparatus; 310: differential information input part; 320: user private key storage part; 330: differential information encoding part; 340: search query generation part; 350: genetic information obtainment part; 360: data decryption part; 400: data center; 410: storage request processing part; 420: encrypted data storage part; 430: encrypted tag storage part; 440: search request processing part; 450: public parameter storage part; 460: access authority storage part; and 500: network.

The invention claimed is:

1. A genetic information storage apparatus which makes a storage apparatus store genetic information, the genetic information storage apparatus comprising:
a computer processor; and
a memory storing a program which, when executed by the computer processor, performs a first process comprising,
obtaining a reference gene which is predefined genetic information;
receiving as input a target gene which is the genetic information to be stored in the storage apparatus;
comparing the obtained reference gene with the received target gene received to generate differential information;
encrypting the target gene to generate an encrypted gene;
generating a tag in which the generated differential information is embedded;
encrypting the generated tag to generate an encrypted tag; and
causing the storage apparatus to store the generated encrypted gene in relation to the generated encrypted tag,
wherein the stored encrypted target gene is searched according to a second process in which an external computer:
decrypts the encrypted tag stored in relation to the encrypted target gene,
extracts the generated differential information from the decrypted tag,
compares the extracted differential information to a keyword received in a search query to determine whether the extracted differential information and the keyword are the same, and
in case the extracted differential information and the keyword are determined to be the same, designates the encrypted target gene as a search match,
wherein, according to the second process, no part of the target gene is exposed to the external computer in unencrypted form during the search, and the search is conducted by the external computer without use of a search index descriptive of the target gene, thereby preserving privacy of information corresponding to the target gene.

2. The genetic information storage apparatus of claim 1, wherein
the differential information includes information of a plurality of types, and
the first process further comprises:
dividing possible values of predefined types included in the differential information into a plurality of blocks, and substituting a value of the type in the generated differential information with identifying information identifying a block to which the value belongs, and
the differential information with the substituted value is encrypted to generate the encrypted tag.

3. The genetic information storage apparatus of claim 2, wherein
the possible values of the types are divided into a plurality of blocks so that a part of the values belonging to each block should also belong to another block, and the value of the types in the generated differential information is substituted with the identifying information identifying each block to which the value belongs to.

4. The genetic information storage apparatus of claim 1, wherein
the encrypted tag is generated by setting, when a cipher attribute set in encrypted data does not correspond to a key attribute set in a private key, based on an encryption scheme according to which the encrypted data is not decrypted by the private key, attribute information of a user who is allowed to search the encrypted gene and the differential information as the cipher attribute, and encrypting a random number value.

5. The genetic information storage apparatus of claim 4, wherein the encrypted gene is generated by setting, based on the encryption scheme, attribute information of a user who is allowed to decrypt the encrypted gene as the cipher attribute, and encrypting the target gene.

6. A genetic information search apparatus which searches genetic information stored in a storage apparatus managed by a data management apparatus, the genetic information search apparatus comprising:
a computer processor; and
a memory storing a program which, when executed by the computer processor, performs a first process comprising,
receiving as input differential information of the genetic information to be searched with a reference gene which is predefined genetic information;

generating a search query in which the differential information received by the differential information input part is embedded; and sending the generated search query to the data management apparatus, and obtaining the genetic information including the differential information, wherein the genetic information stored in the storage apparatus includes an encrypted target gene stored in relation to a tag, which is embedded with differential information of the target gene with the reference gene and them encrypted, wherein the search query is used to search the genetic information stored in the storage apparatus according to a second process in which an external computer:

extracts the differential information from the search query, decrypts the encrypted tag stored in relation to the encrypted target gene, and extracts the differential information from the decrypted tag, performs a comparison to determine whether the differential information from the search query is the same as the differential information extracted from the decrypted tag, and in case the differential information from the search query and the decrypted tag are determined to be the same, designates the encrypted target gene as a search match, wherein, according to the second process, no part of the target gene is exposed to the external computer in unencrypted form during the search, and the search is conducted by the external computer without use of a search index descriptive of the target gene, thereby preserving privacy of information corresponding to the target gene.

7. The genetic information search apparatus of claim 6, wherein the differential information includes information of a plurality of types, the first process further comprises:

dividing possible values of predefined types included in the differential information into a plurality of blocks, and substituting a value of the type in the differential information with identifying information identifying a block to which the value belongs, and the differential information with the substituted value is embedded in the generated search query.

8. The genetic information search apparatus of claim 7, wherein the possible values of predefined types are divided into a plurality of blocks so that a part of the values belonging to each block is made to belong to another block, and the value of the types in the generated differential information is substituted with identifying information identifying each block to which the value belongs.

9. The genetic information search apparatus of claim 6, wherein the first process further comprises:

managing, when a cipher attribute set in encrypted data does not correspond to a key attribute set in a private key, a private key of an encryption scheme according to which the encrypted data is not able to be decrypted by the private key, the private key in which attribute information of a user being set as the key attribute, wherein the differential information is added as a key attribute of the managed private key to generate the search query.

10. The genetic information search apparatus of claim 9, wherein the first process further comprises:

setting, according to the encryption scheme, attribute information of a user who is allowed to decrypt as the cipher attribute, and obtaining an encrypted gene which is the encrypted genetic information as genetic information including the differential information, and decrypting the encrypted gene using the private key managed by the user private key management part.

11. A non-transitory computer readable medium on which is stored a genetic information storage program which makes a storage apparatus store genetic information, the genetic information storage program being executed by a computer to perform:

a reference gene obtainment process to obtain a reference gene which is predefined genetic information;

a gene input process to receive a target gene which is the genetic information to be stored in the storage apparatus;

a difference generation process to compare the reference gene obtained by the reference gene obtainment process with the target gene received by the gene input process to generate differential information, a data encryption process to encrypt the target gene to generate an encrypted gene;

an encrypted tag generation process to generate a tag in which the differential information generated by the difference generation process is embedded, and encrypt the tag to generate the encrypted tag; and a data storage process to make the storage apparatus store the encrypted gene generated by the data encryption process in relation to the encrypted tag generated by the encrypted tag generation process, wherein the stored encrypted target gene is searched according to a search process in which an external computer:

decrypts the encrypted tag stored in relation to the encrypted target gene, extracts the generated differential information from the decrypted tag, compares the extracted differential information to a keyword received in a search query to determine whether the extracted differential information and the keyword are the same, and in case the extracted differential information and the keyword are determined to be the same, designates the encrypted target gene as a search match, wherein, according to the search process, no part of the target gene is exposed to the external computer in unencrypted form during the search, and the search is conducted by the external computer without use of a search index descriptive of the target gene, thereby preserving privacy of information corresponding to the target gene.

12. The non-transitory computer readable medium of claim 11, wherein the differential information includes information a plurality of types, the genetic information storage program further causes the computer to execute:

a differential information substitution process to divide possible values of predefined types included in the differential information into a plurality of blocks, and substitutes a value of the type in the differential information generated by the difference generation process with identifying information identifying a block to which the value belongs, and the encrypted tag generation process encrypts the differential information substituted by the substitution process to generate an encrypted tag.

13. The non-transitory computer readable medium of claim 12, wherein the differential information substitution process divides the possible values of the types into a plurality of blocks so that a part of the values belonging to each block should also belong to another block, and substitutes the value of the types in the differential information generated by the differential information generation process with the identifying information identifying each block to which the value belongs to.

14. The non-transitory computer readable medium of claim 11, wherein the encrypted tag generation process sets, when a cipher attribute set in encrypted data does not correspond to a key attribute set in a private key, based on an encryption scheme according to which the encrypted data is not decrypted by the private key, attribute information of a user who is allowed to search the encrypted gene and the differential information as the cipher attribute, and encrypts a random number value, to generate the encrypted tag.

15. The non-transitory computer readable medium of claim 14, wherein the executed genetic information storage program sets, based on the encryption scheme, attribute information of a user who is allowed to decrypt the encrypted gene as the cipher attribute, and encrypts the target gene, to generate the encrypted gene.

16. A non-transitory computer readable medium on which is stored a genetic information search program which searches genetic information stored in a storage apparatus managed by a data management apparatus, the genetic information search program being executed by a computer to perform:

a differential information input process to receive differential information of the genetic information to be searched with a reference gene which is predefined genetic information;

a search query generation process to generate a search query in which the differential information received by the differential information input process is embedded; and a genetic information obtainment process to send the search query generated by the search query generation process to the data management apparatus, and obtains the genetic information including the differential information, wherein the genetic information stored in the storage apparatus includes an encrypted target gene stored in relation to a tag, which is embedded with differential information of the target gene with the reference gene and them encrypted, wherein the search query is used to search the genetic information stored in the storage apparatus according to a search process in which an external computer:

extracts the differential information from the search query, decrypts the encrypted tag stored in relation to the encrypted target gene, and extracts the differential information from the decrypted tag, performs a comparison to determine whether the differential information from the search query is the same as the differential information extracted from the decrypted tag, and in case the differential information from the search query and the decrypted tag are determined to be the same, designates the encrypted target gene as a search match, wherein, according to the search process, no part of the target gene is exposed to the external computer in unencrypted form during the search, and the search is conducted by the external computer without use of a search index descriptive of the target gene, thereby preserving privacy of information corresponding to the target gene.

17. The non-transitory computer readable medium of claim 16 wherein the differential information includes a plurality of types of information, the genetic information search program further comprises:

a differential information substitution process to divide possible values of predefined types included in the differential information into a plurality of blocks, and substitutes a value of the type in the differential information with identifying information identifying a block to which the value belongs, and the search query generation process generates a search query in which the differential information substituted by the differential information substitution process is embedded.

18. The non-transitory computer readable medium of claim 17, wherein the differential information substitution process divides the possible values of predefined types into a plurality of blocks so that a part of the values belonging to each block is made to belong to another block, and substitutes the value of the types in the differential information with identifying information identifying each block to which the value belongs.

19. The non-transitory computer readable medium of claim 16, wherein execution of the genetic information search program further by the computer further performs:

a user private key management process to manage, when a cipher attribute set in encrypted data does not correspond to a key attribute set in a private key, a private key of an encryption scheme according to which the encrypted data is not able to be decrypted by the private key, the private key in which attribute information of a user being set as the key attribute, and the search query generation process adds the differential information as a key attribute of the private key managed by the user private key management process, to generate the search query.

20. The non-transitory computer readable medium of claim 19, wherein the genetic information obtainment process sets, according to the encryption scheme, attribute information of a user who is allowed to decrypt as the cipher attribute, obtains encrypted gene which is the encrypted genetic information as genetic information including the differential information, and execution of the genetic information search program by the computer further performs:

a decryption process to decrypt the encrypted gene using the private key managed by the user private key management process.

21. A genetic information storage method which makes a storage apparatus store genetic information, the genetic information storage method comprising executing a program in a computer processor to:

obtain a reference gene which is predefined genetic information;

receive as input a target gene which is the genetic information to be stored in the storage apparatus;

compare the obtained reference gene with the received target gene to generate differential information;

encrypt the target gene to generate an encrypted gene;

generate a tag in which the generated differential information is embedded;

encrypt the tag to generate an encrypted tag; and cause the storage apparatus to store the generated encrypted gene in relation to the encrypted tag generated by the encrypted tag generation step, wherein the stored encrypted target gene is searched according to a second process in which an external computer:

decrypts the encrypted tag stored in relation to the encrypted target gene, extracts the generated differential information from the decrypted tag, compares the extracted differential information to a keyword received in a search query to determine whether the extracted differential information and the keyword are the same, and in case the extracted differential information and the keyword are determined to be the same, designates the encrypted target gene as a search match, wherein, according to the second process, no part of the target gene is exposed to the external computer in unencrypted form during the search, and the search is conducted by the external computer without use of a search index descriptive of the target gene, thereby preserving privacy of information corresponding to the target gene.

22. A genetic information search system having a genetic information storage apparatus which makes a storage apparatus managed by a data management apparatus store genetic information and a genetic information search apparatus which searches genetic information including a search keyword from the genetic information that is made to store by the genetic information storage apparatus, wherein the genetic information storage apparatus comprises:

a computer processor, and a memory storing a program which, when executed by the computer processor, performs a process comprising, obtaining a reference gene which is predefined genetic information;

receiving as input a target gene which is the genetic information to be stored in the storage apparatus;

comparing the obtained reference gene with the received target gene to generate differential information;

encrypting the target gene and to generate an encrypted gene;

generating an encrypted tag in which the generated differential information is embedded; and causing the storage apparatus to store the generated encrypted gene in relation to the generated encrypted tag, wherein the genetic information search apparatus comprises:

a second computer processor; and a second memory storing a program which, when executed by the second computer processor, performs a second process comprising, receiving as input differential information of the genetic information to be searched with a reference gene which is predefined genetic information;

generating a search query in which the received differential information is embedded; and sending the generated search query to the data management apparatus, and obtaining the genetic information including the differential information, wherein the stored encrypted target gene is searched according to a search process in which an external apparatus with a third computer processor:

decrypts the encrypted tag stored in relation to the encrypted target gene, extracts the generated differential information from the decrypted tag, compares the extracted differential information to a keyword received in a search query to determine whether the extracted differential information and the keyword are the same, and in case the extracted differential information and the keyword are determined to be the same, designates the encrypted target gene as a search match, wherein, according to the search process, no part of the target gene is exposed to the external apparatus in unencrypted form during the search, and the search is conducted by the external apparatus without use of a search index descriptive of the target gene, thereby preserving privacy of information corresponding to the target gene.

* * * * *